US010358680B2

(12) United States Patent
Vo-Dinh et al.

(10) Patent No.: US 10,358,680 B2
(45) Date of Patent: Jul. 23, 2019

(54) NANO-PLASMONIC MOLECULAR PROBES FOR PLASMONICS COUPLING INTERFERENCE

(71) Applicant: Duke University, Durham, NC (US)

(72) Inventors: Tuan Vo-Dinh, Chapel Hill, NC (US); Hsin-Neng Wang, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 15/442,731

(22) Filed: Feb. 27, 2017

(65) Prior Publication Data
US 2017/0321280 A1 Nov. 9, 2017

Related U.S. Application Data

(62) Division of application No. 14/024,565, filed on Sep. 11, 2013, now abandoned.

(60) Provisional application No. 61/699,381, filed on Sep. 11, 2012.

(51) Int. Cl.
C07H 21/04 (2006.01)
C12Q 1/6886 (2018.01)
C12Q 1/6816 (2018.01)

(52) U.S. Cl.
CPC ......... C12Q 1/6886 (2013.01); C12Q 1/6816 (2013.01)

(58) Field of Classification Search
None
See application file for complete search history.

(56) References Cited

U.S. PATENT DOCUMENTS

| 7,285,835 | B2* | 10/2007 | Rizzo | H01L 43/08 257/295 |
| 7,699,979 | B2* | 4/2010 | Li | B82Y 15/00 210/138 |
| 7,951,535 | B2 | 5/2011 | Vo-Dinh | |
| 8,045,152 | B2 | 10/2011 | Halas et al. | |
| 2007/0212695 | A1* | 9/2007 | Aivazachvili | C12Q 1/6827 435/6.12 |
| 2008/0266555 | A1 | 10/2008 | Murphy et al. | |
| 2009/0017480 | A1 | 1/2009 | Porter et al. | |
| 2009/0023135 | A1* | 1/2009 | Sun | G01N 21/658 435/6.11 |
| 2009/0137418 | A1 | 5/2009 | Miller et al. | |
| 2009/0303461 | A1 | 12/2009 | Sun et al. | |
| 2010/0234579 | A1* | 9/2010 | Mirkin | C07H 21/00 530/391.1 |
| 2010/0254911 | A1 | 10/2010 | Sharma et al. | |
| 2011/0052671 | A1 | 3/2011 | Zasadzinski et al. | |
| 2011/0223257 | A1* | 9/2011 | Zhao | A61K 9/1272 424/502 |
| 2011/0269148 | A1 | 11/2011 | Huang et al. | |
| 2012/0168671 | A1* | 7/2012 | Wang | C09K 11/04 252/62.56 |
| 2012/0177897 | A1* | 7/2012 | Jablonski | B22F 1/0022 428/208 |
| 2012/0225457 | A1* | 9/2012 | Lee | C07H 21/00 435/91.52 |

FOREIGN PATENT DOCUMENTS

WO 2007044057 A2 4/2007
WO 2010009106 A1 1/2010

OTHER PUBLICATIONS

"Viruses" (Wikipedia.com, accessed Nov. 24, 2012).*
"How many species of bacteria are there" (wisegeek.com; accessed Jan. 21, 2014).*
"Fungi," (Wikipedia.com; accessed Jun. 3, 2013).*
"Plant," (Wikipedia.com; accessed Aug. 28, 2015).*
"Mammal," (Wikipedia.com; accessed Sep. 22, 2011).*
"Murinae," (Wikipedia.com, accessed Mar. 18, 2013).*
"Fish," (Wikipedia.com, accessed Nov. 2, 2014).*
"List of sequenced bacterial genomes" (Wikipedia.com; accessed Jan. 24, 2014).*
"Viruses" (Wikipedia.com, accessed Nov. 24, 2012). (Year: 2012).*
"Fungi," (Wikipedia.com; accessed Jun. 3, 2013). (Year: 2013).*
"Plant," (Wikipedia.com; accessed Aug. 28, 2015). (Year: 2015).*
"Mammal," (Wikipedia.com; accessed Sep. 22, 2011). (Year: 2011).*
"Murinae," (Wikipedia.com, accessed Mar. 18, 2013). (Year: 2013).*
"Fish," (Wikipedia.com, accessed Nov. 2, 2014). (Year: 2014).*
"List of sequenced bacterial genomes" (Wikipedia.com; accessed Jan. 24, 2014). (Year: 2201).*
"How many species of bacteria are there?", WiseGeek.com, accessed Jan. 21, 2014. (Year: 2014).*
"List of Infectious diseases," Wikipedia.com, accessed Sep. 13, 2018. (Year: 2018).*
Khalil, I. A.; Kogure, K.; Akita, H.; Harashima, H. Pharmacol. Rev. 2006, 58, (1), 32-45.
Lévy, R.; Shaheen, U.; Cesbron, Y. Nano Rev. 2010, 1, 4889.
Lundqvist, M.; Stigler, J.; Elia, G.; Lynch, I.; Cedervall, T.; Dawson, K. A. Proc. Natl. Acad. Sci. U. S. A. 2008, 105, (38), 14265-14270.
Bartczak, D.; Muskens, O. L.; Nitti, S.; Sanchez-Elsner, T.; Millar, T. M.; Kanaras, A. G. Small 2011.

(Continued)

Primary Examiner — Bradley L. Sisson
(74) Attorney, Agent, or Firm — NK Patent Law

(57) ABSTRACT

Plasmonics-active nanoprobes are provided for detection of target biomolecules including nucleic acids, proteins, and small molecules. The nucleic acids that can be detected include RNA, DNA, mRNA, microRNA, and small nucleotide polymorphisms (SNPs). The nanoprobes can be used in vito in sensitive detection methods for diagnosis of diseases and disorders including cancer. Multiplexing can be performed using the nanoprobes such that multiple targets can be detected simultaneously in a single sample. The methods of use of the nanoprobes include detection by a visible color change. The nanoprobes can be used in vivo for treatment of undesireable cells in a subject.

14 Claims, 14 Drawing Sheets
Specification includes a Sequence Listing.

(56) References Cited

OTHER PUBLICATIONS

Torchilin, V. P. Adv. Drug Delivery Rev. 2008, 60, (4-5), 548-558.
Wei, Y.; Jana, N. R.; Tan, S. J.; Ying, J. Y. Bioconjugate Chem. 2009, 20, (9), 1752-1758.
Zhao, M.; Kircher, M. F.; Josephson, L.; Weissleder, R. Bioconjugate Chem. 2002, 13, (4), 840-844.
Rao, K. S.; Reddy, M. K.; Horning, J. L.; Labhasetwar, V. Biomaterials 2008, 29, (33), 4429-4438.
Tian, X.-H.; Wei, F.; Wang, T.-X.; Wang, D.; Wang, J.; Lin, X.-N.; Wang, P.; Ren, L. Mater. Lett. 2012, 68, 94-96.
Wadia, J. S.; Stan, R. V.; Dowdy, S. F. Nat. Med. 2004, 10, (3), 310-315.
Ruan, G.; Agrawal, A.; Marcus, A. I.; Nie, S. J. Am. Chem. Soc. 2007, 129, (47), 14759-14766.
Pallaoro, A.; Braun, G. B.; Moskovits, M. Proc. Natl. Acad. Sci. U. S. A. 2011, 108, (40), 16559-16564.
Gregas, M. K.; Scaffidi, J. P.; Lauly, B.; Vo-Dinh, T. Surface-Enhanced Raman Scattering Detection and Tracking of Nanoprobes: Enhanced Uptake and Nuclear Targeting in Single Cells. Appl. Spectrosc. 2010, 64, (8), 358-866.
Lewin, M.; Carlesso, N.; Tung, C. H.; Tang, X. W.; Cory, D.; Scadden, D. T.; Weissleder, R. Nat. Biotechnol. 2000, 18, (4), 410-414.
Krpetic, Z.; Saleemi, S.; Prior, I. A.; Sée, V.; Qureshi, R.; Brust, M. ACS Nano 2011, 5, (6), 5195-5201.
Berry, C. C.; De La Fuente, J. M.; Mullin, M.; Chu, S. W. L.; Curtis, A. S. G. IEEE Trans. Nanobioscience 2007, 6, (4), 262-269.
Durr, N. J.; Weisspfennig, C. T.; Holfeld, B. A.; Ben-Yakar, A. J. Biomed. Opt. 2011, 16, (2), 026008.
Pan, L.; He, Q.; Liu, J.; Chen, Y.; Ma, M.; Zhang, L.; Shi, J. J. Am. Chem. Soc. 2012, 120320133341008.
Panté, N.; Kann, M. Mol. Biol. Cell 2002, 13, (2), 425-434.
Mishra, A.; Lai, G. H.; Schmidt, N. W.; Sun, V. Z.; Rodriguez, A. R.; Tong, R.; Tang, L.; Cheng, J.; Deming, T. J.; Kamei, D. T.; Wong, G. C. L. Proc. Natl. Acad. Sci. U. S. A. 2011, 108, (41), 16883-16888.
Zhang, L. W.; Monteiro-Riviere, N. A. Toxicol. Sci. 2009, 110, (1), 138-155.
Iversen, T.-G.; Skotland, T.; Sandvig, K. Nano Today 2011, 6, (2), 176-185.
Chen S, Wang ZL, Ballato J, Foulger SH, Carroll DL. J Am Chem Soc. Dec. 31, 2003;125(52):16186-7.
Hao F, Nehl CL, Hafner JH, Nordlander P. Nano Lett. Mar. 2007;7(3):729-32.
Senthil Kumar P, Pastoriza-Santos I, Rodríguez-González B, Garcia De Abajo FJ, Liz-Marzán LM. Nanotechnology. 2008;19(1):015606-12.
Steel, A. B.; Herne, T. M.; Tarlov, M. J. Anal. Chem. 1998, 70, 4670-7.
Herne, T. M.; Tarlov, M. J. J. Am. Chem. Soc. 1997, 119, 8916-20.
Burgess, J. D.; Hawkridge, F. M. Langmuir 1997, 13, 3781-6.
Boncheva, M.; Scheibler, L.; Lincoln, P.; Vogel, H.; Akerman, B. Langmuir 1999, 15, 4317-20.
Kneipp, J.; Kneipp, H.; Wittig, B.; Kneipp, K. Following the Dynamics of pH in Endosomes of Live Cells with SERS Nanosensors†. J. Phys. Chem. C 2010, 114, (16), 7421-7426.
Potyrailo RA, Conrad RC, Ellington AD, Hieftje GM. Anal Chem. American Chemical Society; Aug. 1998;70(16):3419-25.
Hainfeld et al., The British Journal of Radiology, 79, 248, 2006.
James F Hainfeld, Daniel N Slatkin and Henry M Smilowitz, The use of gold nanoparticles to enhance radiotherapy in mice, Phys. Med. Biol. 49, 2004.
Sang Hyun Cho, Estimation of tumour dose enhancement due to gold nanoparticles during typical radiation treatments: a preliminary Monte Carlo study, Phys. Med. Biol. 50, 2005.
Minelli, C.; Lowe, S. B.; Stevens, M. M., Engineering Nanocomposite Materials for Cancer Therapy, Small 2010, 6, (21), 2336-2357.
Janib, S. M.; Moses, A. S.; MacKay, J. A. Imaging and drug delivery using theranostic nanoparticles, Adv. Drug Deliver. Rev. 2010, 62, (11), 1052-1063.
Lammers, T.; Kiessling, F.; Hennink, W. E.; Storm, G., Nanotheranostics and Image-Guided Drug Delivery: Current Concepts and Future Directions, Mol. Pharm. 2010, 7, (6), 1899-1912.
Xie, J.; Lee, S.; Chen, X., Nanoparticle-based theranostic agents, Adv. Drug Deliver. Rev. 2010, 62, (11), 1064-1079.
Mura, S.; Couvreur, P., Nanotheranostics for personalized medicine, Adv Drug Deliv Rev 2012, 64, (13), 1394-416.
Vo-Dinh, T.; Hiromoto, M. Y. K.; Begun, G. M.; Moody, R. L., Surface-enhanced Raman spectrometry for trace organic analysis, Anal. Chem. 1984, 56, (9), 1667-1670.
Vo-Dinh, T.; Meier, M.; Wokaun, A., Surface-enhanced Raman spectrometry with silver particles on stochastic-post substrates, Anal. Chim. Acta. 1986, 181, (0), 139-148.
Vo-Dinh, T., Surface-enhanced Raman spectroscopy using metallic nanostructures. Trends Analyt. Chem, 1998, 17, (8-9), 557-582.
Vo-Dinh, T.; Dhawan, A.; Norton, S. J.; Khoury, C. G.; Wang, H.-N.; Misra, V.; Gerhold, M.D., Plasmonic Nanoparticles and Nanowires: Design, Fabrication and Application in Sensing†, J. Phys. Chem. C 2010, 114, (16), 7480-7488.
Fales, A. M.; Yuan, H.; Vo-Dinh, T. Silica-Coated Gold Nanostars for Combined Surface-Enhanced Raman Scattering (SERS) Detection and Singlet-Oxygen Generation: A Potential Nanoplatform for Theranostics. Langmuir 2011, 27, (19), 12186-12190.
Yuan, H.; Fales, A. M.; Vo-Dinh, T. TAT Peptide-Functionalized Gold Nanostars: Enhanced Intracellular Delivery and Efficient NIR Photothermal Therapy Using Ultralow Irradiance. J. Am. Chem. Soc. 2012, 134, (28), 11358-11361.
Yuan, H.; Khoury, C. G.; Wilson, C. M.; Grant, G. A.; Bennett, A. J.; Vo-Dinh, T. In vivo particle tracking and photothermal ablation using plasmon-resonant gold nanostars. Nanomedicine 2012, 8, (8), 1355-63.
Bálint, Š.; Rao, S.; Marro, M.; Miškovský; Petrov, D. Monitoring of local pH in photodynamic therapy-treated live cancer cells using surface-enhanced Raman scattering probes. J. Raman Spectrosc. 2011, 42, (6), 1215-1221.
Kircher, M. F.; De La Zerda, A.; Jokerst, J. V.; Zavaleta, C. L.; Kempen, P. J.; Mittra, E.; Pitter, K.; Huang, R.; Campos, C.; Habte, F.; Sinclair, R.; Brennan, C. W.; Mellinghoff, I. K.; Holland, E. C.; Gambhir, S. S. A brain tumor molecular imaging strategy using a new triple-modality MRI-photoacoustic-Raman nanoparticle. Nat Med 2012, 18, (5), 829-834.
Alvarez-Puebla, R. A.; Liz-Marzán, L. M. SERS-Based Diagnosis and Biodetection. Small 2010, 6, (5), 604-610.
"List of sequences bacterial genomes", (Wikipedia.com; accessed Jan. 24, 2014).
Kneipp, J.; Kneipp, H.; Rice, W. L.; Kneipp, K. Optical Probes for Biological Applications Based on Surface-Enhanced Raman Scattering from Indocyanine Green on Gold Nanoparticles. Anal. Chem. 2005, 77, (8), 2381-2385.
Kneipp, J.; Kneipp, H.; Rajadurai, A.; Redmond, R. W.; Kneipp, K. Optical probing and imaging of live cells using SERS labels. J. Raman Spectrosc. 2009, 40, (1), 1-5.
Qian, X. M.; Nie, S. M. Single-molecule and single-nanoparticle SERS: from fundamental mechanisms to biomedical applications. Chem. Soc. Rev. 2008, 37, (5), 912-920.
Faulds, K.; Smith, W. E.; Graham D. Evaluation of Surface-Enhanced Resonance Raman Scattering for Quantitative DNA Analysis. Anal. Chem. 2003, 76, (2), 412-417.
Rodriguez-Lorenzo, L.; Krpetic, Z.; Barbosa, S.; Alvarez-Puebla, R. A.; Liz-Marzan, L. M.; Prior, I. A.; Brust, M. Intracellular mapping with SERS-encoded gold nanostars. Integr. Biol. 2011, 3, (9), 922-926.
Küstner, B.; Gellner, M.; Schütz, M.; Schöppler, F.; Marx, A.; Ströbel, P.; Adam, P.; Schmuck, C.; Schlücker, S. SERS Labels for Red Laser Excitation: Silica-Encapsulated SAMs on Tunable Gold/Silver Nanoshells. Angew. Chem. Int. Edit. 2009, 48, (11), 1950-1953.

(56) References Cited

OTHER PUBLICATIONS

Cao, Y. C.; Jin, R.; Nam, J.-M.; Thaxton, C. S.; Mirkin, C. A. Raman Dye-Labeled Nanoparticle Probes for Proteins. J. Am. Chem. Soc. 2003, 125, (48), 14676-14677.

Wang, G.; Park, H.-Y.; Lipert, R. J.; Porter, M. D. Mixed Monolayers on Gold Nanoparticle Labels for Multiplexed Surface-Enhanced Raman Scattering Based Immunoassays. Anal. Chem. 2009, 81, (23), 9643-9650.

Gregas, M. K.; Yan, F.; Scaffidi, J.; Wang, H.-N.; Vo-Dinh, T. Characterization of nanoprobe uptake in single cells: spatial and temporal tracking via SERS labeling and modulation of surface charge. Nanomedicine: NBM 2011, 7, (1), 115-122.

Zavaleta, C. L.; Smith, B. R.; Walton, I.; Doering, W.; Davis, G.; Shojaei, B.; Natan, M. J.; Gambhir, S. S. Multiplexed imaging of surface enhanced Raman scattering nanotags in living mice using noninvasive Raman spectroscopy. Proc. Natl. Acad. Sci. U S A 2009, 106, (32), 13511-13516.

Keren, S.; Zavaleta, C.; Cheng, Z.; De La Zerda, A.; Gheysens, O.; Gambhir, S. S. Noninvasive molecular imaging of small living subjects using Raman spectroscopy. Proc. Natl. Acad. Sci. U S A 2008, 105, (15), 5844-5849.

Kim, J.-H.; Kim, J.-S.; Choi, H.; Lee, S.-M.; Jun, B.-H.; Yu, K.-N.; Kuk, E.; Kim, Y.-K.; Jeong, D. H.; Cho, M.-H.; Lee, Y.-S. Nanoparticle Probes with Surface Enhanced Raman Spectroscopic Tags for Cellular Cancer Targeting. Anal. Chem. 2006, 78, (19), 6967-6973.

Lam, M.; Oleinick, N. L.; Nieminen, A.-L. Photodynamic Therapy-induced Apoptosis in Epidermoid Carcinoma Cells. J. Biol. Chem. 2001, 276, (50), 47379-47386.

Tang, W.; Xu, H.; Kopelman, R.; Philbert, M. A. Photodynamic Characterization and In Vitro Application of Methylene Blue-containing Nanoparticle Platforms. Photochem. Photobiol. 2005, 81, (2), 242-249.

Rossi, L. M.; Silva, P. R.; Vono, L. L. R.; Fernandes, A. U.; Tada, D. B.; Baptista, M. C. S. Protoporphyrin IX Nanoparticle Carrier: Preparation, Optical Properties, and Singlet Oxygen Generation. Langmuir 2008, 24, (21), 12534-12538.

Lee, S. J.; Koo, H.; Lee, D.-E.; Min, S.; Lee, S.; Chen, X.; Choi, Y.; Leary, J. F.; Park, K.; Jeong, S. Y.; Kwon, I. C.; Kim, K.; Choi, K. Tumor-homing photosensitizer-conjugated glycol chitosan nanoparticles for synchronous photodynamic imaging and therapy based on cellular on/off system. Biomaterials 2011, 32, (16), 4021-4029.

Bechet, D.; Couleaud, P.; Frochot, C.; Viriot, M.-L.; Guillemin, F.; Barberi-Heyob, M. Nanoparticles as vehicles for delivery of photodynamic therapy agents. Trends Biotechnol. 2008, 26, (11), 612-621.

Roy, I.; Ohulchanskyy, T. Y.; Pudavar, H. E.; Bergey, E. J.; Oseroff, A. R.; Morgan, J.; Dougherty, T. J.; Prasad, P. N. Ceramic-Based Nanoparticles Entrapping Water-Insoluble Photosensitizing Anticancer Drugs: A Novel Drug-Carrier System for Photodynamic Therapy. J. Am. Chem. Soc. 2003, 125, (26), 7860-7865.

USPTO, Final Rejection for U.S. Appl. No. 13/888,226, dated Jun. 28, 2016.

USPTO, Non-Final Rejection for U.S. Appl. No. 13/971,822, dated Jun. 15, 2016.

USPTO, Non-Final Rejection for U.S. Appl. No. 14/861,353, dated Sep. 1, 2016.

Wang and Vo-Dinh. Multiplex detection of breast cancer biomarkers using plasmonic molecular sentinel nanoprobes. Nanotechnology. Feb. 11, 2009; 20(6).

Buzdin et al., Stem-Loop Oligonucleotides as Hybridization Probes and Their Practical Use in Molecular Biology and Biomedicine. Ch 4, pp. 85-96., in book: Nucleic Acids Hybridization Modern Applications, 2007, Springer Press.

USPTO, Restriction Requirement for U.S. Appl. No. 13/888,226, dated Nov. 5, 2015.

Hlrelescu et al.: "Single gold nanostars enhance Raman scattering", 2009, Appl. Phys. Lett. 94: 153113, 3 pages.

Dondapati et al.: Label-free biosensing based on single gold nanostarts as plasmonic transducers:, 2010, ACS Nano 4: 6318-6322.

USPTO, Non-Final Rejection for U.S. Appl. No. 13/888,226, dated Jan. 11, 2016.

Schütz et al.: "Hydrophilically stabilized gold nanostars as SERS labels for tissue imaging of the tumor suppressor p63 by immuno-SERS microscopy", 2011, Chem. Commun. 47: 4216-4218, Published online Feb. 28, 2011.

Alric et al.: "Gadolinium chelate coated gold nanoparticles as contrast agents for both X-ray computed tomography and magnetic resonance imaging", 2008, J. Am. Chem. Soc. 130: 5908-5915.

Jang et al.: "Gold nanorod-photosensitizer complex for near-infrared fluorescence imaging and photodynamic/photothermal therapy in vivo", 2011, ACS Nano 5: 1086-1094, Published online Jan. 18, 2011.

ISA/KR, International Search Report and Written Opinion for PCT patent application PCT/US2013/059312, dated Dec. 5, 2013.

Rodriguez-Lorenzo et al.: "Plasmonic nanosensors with inverse sensitivity by means of enzyme-guided crystal growth", Nature Materials, May 27, 2012, vol. 11, No. 7, pp. 604-607.

Ohulchanskyy, T. Y.; Roy, I.; Goswami, L. N.; Chen, Y.; Bergey, E. J.; Pandey, R. K.; Oseroff, A. R.; Prasad, P. N. Organically Modified Silica Nanoparticles with Covalently Incorporated Photosensitizer for Photodynamic Therapy of Cancer. Nano Lett. 2007, 7, (9), 2835-2842.

Kim, S.; Ohulchanskyy, T. Y.; Pudavar, H. E.; Pandey, R. K.; Prasad, P. N. Organically Modified Silica Nanoparticles Co-encapsulating Photosensitizing Drug and Aggregation-Enhanced Two-Photon Absorbing Fluorescent Dye Aggregates for Two-Photon Photodynamic Therapy. J. Am. Chem. Soc. 2007, 129, (9), 2669-2675.

Yan, F.; Kopelman, R. The Embedding of Meta-tetra(Hydroxyphenyl)-Chlorin into Silica Nanoparticle Platforms for Photodynamic Therapy and Their Singlet Oxygen Production and pH-dependent Optical Properties. Photochem. Photobiol. 2003, 78, (6), 587-591.

Lu, J.; Liong, M.; Zink, J. I.; Tamanoi, F. Mesoporous Silica Nanoparticles as a Delivery System for Hydrophobic Anticancer Drugs. Small 2007, 3, (8), 1341-1346.

Yuan, H.; Fales, A. M.; Khoury, C. G.; Liu, J.; Vo-Dinh, T., J. Raman Spectrosc. 2012.

Fernández-López, C.; Mateo-Mateo, C.; Álvarez-Puebla, R. N. A.; Pérez-Juste, J.; Pastoriza-Santos, I.; Liz-Marzán, L. M. Highly Controlled Silica Coating of PEG-Capped Metal Nanoparticles and Preparation of SERS-Encoded Particles†. Langmuir 2009, 25, (24), 13894-13899.

International Search Report dated Dec. 5, 2013 for application PCT/US2013/059312 filed Sep. 11, 2013.

Kievit, F. M.; Zhang, M. Adv. Mater. (Weinheim, Ger.) 2011, 23, (36), H217-47.

Shi, J.; Votruba, A. R.; Farokhzad, O. C.; Langer, R. Nano Lett. 2010, 10, (9), 3223-3230.

Farrell, D.; Alper, J.; Ptak, K.; Panaro, N. J.; Grodzinski, P.; Barker, A. D. ACS Nano 2010, 4, (2), 589-594.

Chadwick, S.; Kriegel, C.; Amiji, M. Adv. Drug Delivery Rev. 2010, 62, (4-5), 394-407.

Riehemann, K.; Schneider, S. W.; Luger, T. A.; Godin, B.; Ferrari, M.; Fuchs, H. Angew. Chem., Int. Ed. Engl. 2009, 48, (5), 872-897.

Wang, X.; Yang, L.; Chen, Z. G.; Shin, D. M. CA Cancer J Clin 2008, 58, (2), 97-110.

Nie, S.; Xing, Y.; Kim, G. J.; Simons, J. W. Annu. Rev. Biomed. Eng. 2007, 9, 257-288.

Hahn, M. A.; Singh, A. K.; Sharma, P.; Brown, S. C.; Moudgil, B. M. Anal. Bioanal. Chem. 2011, 399, (1), 3-27.

Ghosh, P.; Han, G.; De, M.; Kim, C. K.; Rotello, V. M. Adv. Drug Delivery Rev. 2008, 60, (11), 1307-1315.

Huang, L.; Liu, Y. Annu. Rev. Biomed. Eng. 2011, 13, (1), 507-530.

Juzenas, P.; Chen, W.; Sun, Y.-P.; Neto Coehlo, M. A.; Generalov, R.; Generalova, N.; Christensen, I. L. Adv. Drug Delivery Rev. 2008, 60, (15), 1600-1614.

Kennedy, L. C.; Bickford, L. R.; Lewinski, N. A.; Coughlin, A. J.; Hu, Y.; Day, E. S.; West, J. L.; Drezek, R. A. Small 2011, 7, (2), 169-183.

Ruoslahti, E.; Bhatia, S. N.; Sailor, M. J. J. Cell Biol. 2010, 188, (6), 759-768.

(56) References Cited

OTHER PUBLICATIONS

Peer, D.; Karp, J. M.; Hong, S.; Farokhzad, O. C.; Margalit, R.; Langer, R. Nat. Nanotechnol. 2007, 2, (12), 751-760.

Hu, M.; Chen, J.; Li, Z.-Y.; Au, L.; Hartland, G. V.; Li, X.; Marquez, M.; Xia, Y. Chem. Soc. Rev. 2006, 35, (11), 1084-1094.

Boisselier, E.; Astruc, D. Chem. Soc. Rev. 2009, 38, (6), 1759-1782.

Weissleder, R. Nat. Biotechnol. 2001, 19, (4), 316-317.

Guerrero-Martínez, A.; Barbosa, S.; Pastoriza-Santos, I.; Liz-Marzán, L. M. Curr. Opin. Colloid Interface Sci. 2011, 16, (2), 118-127.

Yuan, H.; Khoury, C. G.; (Co-First Author); Hwang, H.; Wilson, C. M.; Grant, G. A.; Vo-Dinh, T. Nanotechnology 2012, 23, (7), 075102.

Austin, L. A.; Kang, B.; Yen, C.-W.; El-Sayed, M. A. J. Am. Chem. Soc. 2011, 133, (44), 17594-17597.

Tkachenko, A. G.; Xie, H.; Liu, Y.; Coleman, D.; Ryan, J.; Glomm, W. R.; Shipton, M. K.; Franzen, S.; Feldheim, D. L. Bioconjugate Chem. 2004, 15, (3), 482-490.

Tong, L.; Wei, Q.; Wei, A.; Cheng, J.-X. Photochem. Photobiol. 2009, 85, (1), 21-32.

Hutter, E.; Maysinger, D. Microsc. Res. Tech. 2010, 74, (7), 592-604.

Van De Broek, B.; Devoogdt, N.; D'Hollander, A.; Gijs, H.-L.; Jans, K.; Lagae, L.; Muyldermans, S.; Maes, G.; Borghs, G. ACS Nano 2011, 5, (6), 4319-4328.

ANSI, American National Standard for safe use of lasers. Laser Institute of America: Orlando, FL, 2000.

Huang, X.; Kang, B.; Qian, W.; Mackey, M. A.; Chen, R C.; Oyelere, A. K.; El-Sayed, I. H.; El-Sayed, M. A. J. Biomed. Opt 2010, 15, (5), 058002.

Au, L.; Zheng, D.; Zhou, F.; Li, Z.-Y.; Li, X.; Xia, Y. ACS Nano 2008, 2, (8), 1645-1652.

Kim, J.; Park, S.; Lee, J. E.; Jin, S. M.; Lee, J. H.; Lee, I. S.; Yang, I.; Kim, J.-S.; Kim, S. K.; Cho, M.-H.; Hyeon, T. Angew. Chem., Int. Ed. Engl. 2006, 45, (46), 7754-7758.

Patel, L.; Zaro, J.; Shen, W.-C. Pharm. Res. 2007, 24, 1977-1992.

USPTO, Non-Final Office Action for U.S. Appl. No. 15/785,615, dated Feb. 8, 2019.

USPTO, Non-Final Rejection for U.S. Appl. No. 13/971,822, dated Jun. 15, 2015.

USPTO, Non-Final Rejection for U.S. Appl. No. 14/024,565, dated Jan. 20, 2016.

USPTO; Non-Final Office Action for U.S. Appl. No. 13/888,226 dated Jan. 12, 2017.

USPTO; Non-Final Office Action for U.S. Appl. No. 13/888,226 dated Jan. 11, 2016.

USPTO; Final Office Action for U.S. Appl. No. 13/888,226 dated Jun. 28, 2016.

USPTO; Non-Final Office Action for U.S. Appl. No. 15/408,563 dated Sep. 8, 2017.

USPTO; Final Office Action for U.S. Appl. No. 14/024,565 dated Oct. 26, 2016.

USPTO; Non-Final Office Action for U.S. Appl. No. 15/442,731 dated Jul. 28, 2017.

USPTO; Final Office Action for U.S. Appl. No. 15/442,731 dated Sep. 18, 2018.

USPTO; Final Office Action for U.S. Appl. No. 15/442,731 dated Jun. 15, 2018.

USPTO; Non-Final Office Action for U.S. Appl. No. 14/861,353 dated Dec. 21, 2017.

USPTO; Final Office Action for U.S. Appl. No. 14/861,353 dated Jul. 24, 2018.

USPTO; Final Office Action for U.S. Appl. No. 14/861,353 dated Apr. 18, 2017.

USPTO; Restriction Requirement for U.S. Appl. No. 13/971,822 dated Jan. 25, 2016.

USPTO; Restriction Requirement for U.S. Appl. No. 14/024,565 dated Aug. 25, 2015.

USPTO; Restriction Requirement for U.S. Appl. No. 14/861,353 dated Apr. 21, 2016.

USPTO; Non-Final Office Action for U.S. Appl. No. 14/861,353 dated May 30, 2019, 31 pages.

\* cited by examiner

PROBE-NANOPARTICLE       LNA-NANOPARTICLE

PLASMONIC COUPLING

FIG.5A
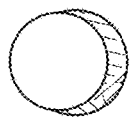
FIG.5B
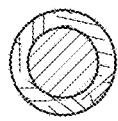
FIG.5C
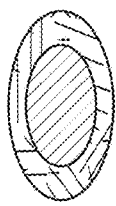
FIG.5D
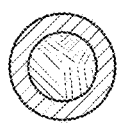
FIG.5E
FIG.5F
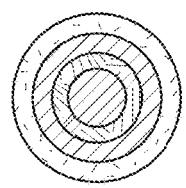
FIG.5G
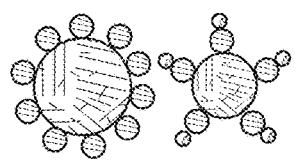
FIG.5H
FIG.5I
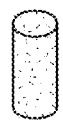
FIG.5J
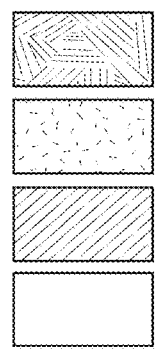
METAL 1 (E.G., AU, AG)
METAL 2 (E.G., AU, AG)
DIELECTRIC MATERIAL
PROACTIVE COATING

SEQUENCE LISTING

```
<160> NUMBER OF SEQ ID NOS: 4

<210> SEQ ID NO 1
<211> LENGTH: 22
<212> TYPE: DNA
<213> ORGANISM: Homo sapiens

<400> SEQUENCE: 1
tcaacatcag tctgataagc ta                                            22

<210> SEQ ID NO 2
<211> LENGTH: 13
<212> TYPE: DNA
<213> ORGANISM: Homo sapiens

<400> SEQUENCE: 2
tagcttatca gac                                                      13

<210> SEQ ID NO 3
<211> LENGTH: 22
<212> TYPE: RNA
<213> ORGANISM: Homo sapiens

<400> SEQUENCE: 3
uagcuuauca gacugauguu ga                                            22
```

```
<210> SEQ ID NO 4
<211> LENGTH: 40
<212> TYPE: DNA
<213> ORGANISM: Homo sapiens

<400> SEQUENCE: 4
tcatccatga caactttggt atcgtggaag gactcatgac                               40
```

NANO-PLASMONIC MOLECULAR PROBES FOR PLASMONICS COUPLING INTERFERENCE

CROSS REFERENCE TO RELATED APPLICATIONS

This application is a divisional of U.S. patent application Ser. No. 14/024,565 entitled "Nano-Plasmonic Molecular Probes for Plasmonics Coupling Interference", filed on Sep. 11, 2013, abandoned, which claims priority to U.S. Provisional Patent Application No. 61/699,381 filed Sep. 11, 2012, the disclosures of which are incorporated herein by reference in their entireties. This application is related to PCT Application Number PCTUS13/59312 filed Sep. 11, 2013, U.S. patent application Ser. No. 13/888,226 filed May 6, 2013, and U.S. patent application Ser. No. 13/971,822 filed Aug. 20, 2013, the disclosures of which are incorporated herein by reference in their entireties.

STATEMENT OF GOVERNMENT SUPPORT

This invention was made with U.S. Government support under the National Institutes of Health grant No. RO1 EB006201, the Defense Advanced Research Projects Agency grant No. DARPA-N66001-09-C-2082, and the Department of Defense grant No. W81XWH-09-1-0064. The U.S. Government has certain rights in the invention.

TECHNICAL FIELD

The present disclosure relates to the use of nanoprobes in plasmonics coupling interference. Particularly, the present disclosure relates to nanoprobes and methods for using the nanoprobes in plasmonics coupling interference as a simple and rapid screening tool for detection and diagnostics.

BACKGROUND

The nano-network plasmonics coupling interference (NPCI) principle is based on the interference of the plasmonics enhancement mechanisms of the electromagnetic field effect. In plasmonics and enhanced electromagnetic fields there are two main o the addition of a field caused by the polarization of the metal particle; (2) in addition to the enhancement of the excitation laser field, there is another enhancement due to the molecule radiating an amplified emission (luminescence, Raman, etc.) field, which further polarizes the metal particle, thereby acting as an antenna to further amplify a Raman/Luminescence signal.

Electromagnetic enhancements are divided into two main classes: a) enhancements that occur only in the presence of a radiation field, and b) enhancements that can occur even in the absence of a radiation field. The first class of enhancements is further divided into several processes. Plasma resonances on the substrate surfaces, also called surface plasmons, provide a major contribution to electromagnetic enhancement. An effective type of plasmonics-active substrate consists of nanostructured metal particles, protrusions, or rough surfaces of metallic materials. Incident light irradiating these surfaces excites conduction electrons in the metal, and induces excitation of surface plasmons leading to Raman/Luminescence enhancement. At the plasmon frequency, the metal nanoparticles (or nanostructured roughness) become polarized, resulting in large field-induced polarizations and thus large local fields on the surface. These local fields increase the Luminescence/Raman emission intensity, which is proportional to the square of the applied field at the molecule. As a result, the effective electromagnetic field experienced by the analyte molecule on theses surfaces is much larger than the actual applied field. This field decreases as $1/r^3$ away from the surface. Therefore, in the electromagnetic models, the luminescence/Raman-active analyte molecule is not required to be in contact with the metallic surface but can be located anywhere within the range of the enhanced local field, which can polarize this molecule. The dipole oscillating at the wavelength $\lambda$ of Raman or luminescence can, in turn, polarize the metallic nanostructures and, if $\lambda$ is in resonance with the localized surface plasmons, the nanostructures can enhance the observed emission light (Raman or luminescence).

Plasmonics-active metal nanoparticles also exhibit strongly enhanced visible and near-infrared light absorption, several orders of magnitude more intense compared to conventional laser phototherapy agents. The use of plasmonic nanoparticles as highly enhanced photoabsorbing agents has thus introduced a much more selective and efficient phototherapy strategy.

One of several phenomena that can enhance the efficiency of light emitted (Raman or luminescence) from molecules adsorbed on or near a metal nanostructure is Raman scatter known as the surface enhanced Raman scattering (SERS) effect. The use of SERS measurement for a variety of chemicals including several homocyclic and heterocyclic polyaromatic compounds has been reported. [T. Vo-Dinh, M. Y. K. Hiromoto, G. M. Begun and R. L. Moody, "*Surface-enhanced Raman spectroscopy for trace organic analysis,*" *Anal. Chem.*, vol. 56, 1667, 1984]. Extensive research has been devoted to understanding and modeling the Raman enhancement in SERS since the mid 1980's. For example, Kerker published models of electromagnetic field enhancements for spherical silver nanoparticles and metallic nanoshells around dielectric cores as far back as 1984 [M. M. Kerker, *Acc. Chem. Res.*, 17, 370 (1984)]. Kerker's work illustrated theoretical calculations of electromagnetic enhancements for isolated spherical nanospheres and nanoshells at different excitation wavelengths. In his calculations, the intensity of the normally weak Raman scattering process was increased by factors as large as $10^{13}$ or $10^{15}$ for compounds adsorbed onto a SERS substrate, allowing for single-molecule detection. As a result of the electromagnetic field enhancements produced near nanostructured metal surfaces, nanoparticles have found increased use as fluorescence and Raman nanoprobes.

The theoretical models indicate that it is possible to tune the size of the nanoparticles and the nanoshells to the excitation wavelength. Experimental evidence suggests that the origin of the $10^6$- to $10^{15}$-fold Raman enhancement primarily arises from two mechanisms: a) an electromagnetic "lightning rod" effect occurring near metal surface structures associated with large local fields caused by electromagnetic resonances, often referred to as "surface plasmons"; and b) a chemical effect associated with direct energy transfer between the molecule and the metal surface.

According to classical electromagnetic theory, electromagnetic fields can be locally amplified when light is incident on metal nanostructures. These field enhancements can be quite large (typically $10^6$- to $10^7$-fold, but up to $10^{15}$-fold enhancement at "hot spots"). When a nanostructured metallic surface is irradiated by an electromagnetic field (e.g., a laser beam), electrons within the conduction band begin to oscillate at a frequency equal to that of the incident light. These oscillating electrons, called "surface plasmons," produce a secondary electric field which adds to the incident field. If these oscillating electrons are spatially confined, as is the case for isolated metallic nanospheres or roughened metallic surfaces (nanostructures), there is a characteristic frequency (the plasmon frequency) at which there is a resonant response of the collective oscillations to the incident field. This condition yields intense localized field enhancements that can interact with molecules on or near the metal surface. In an effect analogous to a "lightning rod," secondary fields are typically most concentrated at points of high curvature on the roughened metal surface. It has been widely accepted that the electromagnetic (EM) enhancement contributes the main part of enormous enhancement factor which greatly increases the intrinsically weak normal Raman scattering cross-section. Theoretical studies of EM effects have shown that the enhanced EM fields are confined within only a tiny region near the surface of the particles, and the SERS enhancement (G) falls off as $G=[r/(r+d)]^{12}$ for a single molecule located a distance d from the surface of a metal nanoparticle of radius r [K. Kneipp, H. Kneipp, I. Itzkan, R. R Dasar, M. S. Feld, *J. phys. Condens. Matter* 14, R597 (2002)]. Thus, the EM enhancement factor G strongly decreases with increased distance between the analyte and metal surface.

In addition to the EM enhancement contributed from individual particles, it has been observed that the EM field is particularly strong in the interstitial space between the particles. It is believed that the anomalously strong Raman signal originates from "hot spots", i.e., regions where clusters of several closely-spaced nanoparticles are concentrated in a small volume. The high-intensity SERS then originates from the mutual enhancement of surface plasmon local electric fields of several nanoparticles that determine the dipole moment of a molecule trapped in a gap between metal surfaces. This effect is also referred to as interparticle coupling or plasmonic coupling in a network of nanoparticles (NPs), and the effect can produce a further enhancement in addition to the enhancement from individual particles. The problem of predicting the electromagnetic field in the gaps between metal nanoparticles under optical illumination has attracted interest in recent years because of the very large field enhancements induced in the particle gaps arising from surface plasmon resonances.

To investigate this feature, the electric field was calculated surrounding a finite chain of metal nanospheres or nanospheroids when illuminated with coherent light [S. J. Norton and T. Vo-Dinh, "Optical response of linear chains of nanospheres and nanospheroids," *J. Opt. Soc. Amer.* 25, 2767-2775 (2007)]. The chain structure consists of nanoparticles aligned closely with small gaps between them. A method was developed applicable to spheres and spheroids which avoided the use of translational formulas at the expense of the numerical, but allowed for straightforward evaluation of certain simple integrals. In this work, the quasi-static approximation was assumed, but the basic approach could be extended to the full-wave problem, in which retardation affects were accounted for. The approach was illustrated by computing the electric field in the gaps between two spheres and between two spheroids over a range of frequencies so that the induced plasmon resonances were evident. At frequencies matching the plasmon resonances, very large field enhancements were observed to occur. It was also demonstrated how the field enhancement varied with the aspect ratio of a prolate spheroid.

Plots were generated showing the calculated values of the magnitude of the electric field between two spheres and between two prolate spheroids with two different aspect ratios. The plots showed the calculated value of the field magnitude over a range of wavelengths at a point on axis in the gap midway between the two particles. The magnitude of the incident electric field was unity; thus, the plots showed the field enhancement relative to the incident field. The observed peaks corresponded to the frequencies of the plasmon resonances. Because of the assumption of a uniform incident electric field (the quasi-static approximation), the enhancement is scale invariant; that is, the enhancement only depends on the ratio of the gap width to the particle size (e.g., the radius of a sphere or, for a spheroid, the lengths of the semi-major and semi-minor axes).

In the calculations, three pairs of particles were compared with different gaps between them: a pair of identical spheres of unit radius, and a pair of prolate spheroids with two different aspect ratios but equal in volume to that of the sphere. It was noted that the plasmon resonance red-shifted with increasing aspect ratio. In addition, for a given gap width, the two spheroids produced a noticeably larger enhancement than the two spheres. This was expected, since the smaller curvature at the spheroid ends creates a larger surface charge density and a larger field. The increased field that was observed at the ends was attributed to the "lighting rod effect." The pair of nanospheres having an aspect ratio of 4 and a 2% gap showed an electric field enhancement in the gap of over 700 at the peak of the plasmon resonance. The total SERS signal was approximately proportional to the fourth power of the electric field magnitude, giving a total SERS enhancement of over $4\times10^{10}$. However, a spatially averaged enhancement would be much less than this observed peak value. [Ref: S. J. Norton and T. Vo-Dinh, "*Optical response of linear chains of nanospheres and nanospheroids,*" *J. Opt. Soc. Amer.* 25, 2767-2775 (2007)].

The development of practical and sensitive techniques for screening nucleic acid biomarkers related to medical diseases and cancers is critical for early diagnosis, prevention and effective interventions. Recent advances in molecular profiling technology have made significant progress in the discovery of various biomarkers. It has been implicated that biomarkers such as single-nucleotide polymorphisms (SNPs) and microRNAs (miRNAs) could serve as important predictors of cancer risk and progression. SNPs are the most common genetic variations which could contribute to disease risk by creating genetic instability. MicroRNAs, a class of small noncoding endogenous RNA molecules, are emerging as promising biomarkers for cancer diagnostics and classification. Fast and precise measurement of SNPs and miRNAs will help identify molecular signatures critical for the evaluation of cancer risk and early detection.

The miRNA is a class of 18-24 nucleotide non-coding RNA molecules found in almost all organisms, including humans, plants, virus and animals. Recent studies revealed that miRNAs exert their gene regulatory function either directly through cleavage of messenger RNA (mRNA) or indirectly through translational repression by binding to their target mRNA strands. It has been shown that miRNAs are involved in many critical biological processes such as development, differentiation, metabolism and tumorigenesis. Moreover, alterations in the expression levels of a single or multiple miRNAs have been shown to be linked with cancer types, disease stages and response to treatment. The miRNA expression profiles may serve as useful tests for cancer and disease diagnostics. In the past years, many miRNA detection methods have been reported. However, the small size of miRNA molecules makes the detection more difficult than working with genomic DNA and mRNA. So far, the most standardized and widely used method to detect miRNA is northern blotting, which is laborious and time-consuming. Thus, there is a strong need to develop a rapid, selective and sensitive method to detect miRNA molecules.

Therefore, new methods and plasmonics-active nanoparticle compositions having improved properties are desireable to take advantage of the interparticle plasmonics coupling described above for detection, diagnostics and therapy.

SUMMARY OF THE INVENTION

In one embodiment, a pair of nanoprobes is provided for detecting nucleic acid targets, the pair comprising a reporter nanoprobe and a capture nanoprobe, wherein the reporter nanoprobe comprises: at least one plasmonic nanoparticle; and an oligonucleotide reporter probe attached at one end to the nanoparticle, the reporter probe having an attached optical label, and wherein the capture nanoprobe comprises: at least one plasmonic nanoparticle; and a capture oligonucleotide attached at one end to the nanoparticle, wherein the capture oligonucleotide is complementary to both the reporter probe and the nucleic acid target, and wherein the capture oligonucleotide hybridizes to the reporter probe in the absence of the nucleic acid target such that plasmonic coupling electromagnetic enhancement occurs between neighboring reporter and capture nanoparticles.

In one embodiment, a method is provided for detecting nucleic acid targets, comprising: incubating a reporter nanoprobe and a capture nanoprobe directed to a nucleic acid target in the presence and the absence of the target under conditions suitable for the target to hybridize with the capture nanoprobe, wherein the reporter nanoprobe comprises: at least one plasmonic nanoparticle; and an oligonucleotide reporter probe attached at one end to the nanoparticle, the reporter probe having an optical label;wherein the capture nanoprobe comprises: at least one plasmonic nanoparticle; and a capture oligonucleotide attached at one end to the nanoparticle, wherein the capture oligonucleotide is complementary to both the reporter probe and the nucleic acid target, and wherein the capture oligonucleotide hybridizes to the reporter probe in the absence of the nucleic acid target such that plasmonic coupling electromagnetic enhancement occurs between neighboring reporter and capture nanoparticles, irradiating the sample with electromagnetic radiation from an excitation source; and detecting the electromagnetic radiation originated by the label, wherein a level of electromagnetic radiation originated by the label in the presence of the target is changed upon hybridization of the capture oliognucleotide to the target.

In one embodiment, a method is provided for treating undesirable cells comprising: contacting an undesirable cell with a reporter nanoprobe and a capture nanoprobe, wherein the reporter nanoprobe comprises: at least one plasmonic nanoparticle; and an oligonucleotide reporter probe attached at one end to the nanoparticle, the reporter probe having an optical label;wherein the capture nanoprobe comprises: at least one plasmonic nanoparticle; and a capture oligonucleotide attached at one end to the nanoparticle, wherein the capture oligonucleotide is complementary to both the reporter probe and the nucleic acid target, and wherein the capture oligonucleotide hybridizes to the reporter probe in the absence of the nucleic acid target such that plasmonic coupling electromagnetic enhancement occurs between neighboring reporter and capture nanoparticles; and irradiating the sample with electromagnetic radiation from an excitation source, wherein the optical label is capable of absorbing electromagnetic radiation from one or both of electromagnetic radiation originated as a result of excitation of the nanoparticle and directly from the excitation radiation, and wherein the undesirable cells are damaged by one or both of thermal energy direct from the radiation and thermal energy emitted as a result of excitation of the nanoparticle.

In one embodiment, a method is provided for detecting nucleic acid targets, comprising: incubating a reporter nanoprobe and a capture nanoprobe directed to a nucleic acid target in the presence and the absence of the target under conditions suitable for the target to hybridize with the capture nanoprobe, wherein the reporter nanoprobe comprises: at least one plasmonic nanoparticle; and an oligonucleotide reporter probe attached at one end to the nanoparticle; wherein the capture nanoprobe comprises: at least one plasmonic nanoparticle; and a capture oligonucleotide attached at one end to the nanoparticle, wherein the capture oligonucleotide is complementary to both the reporter probe and the nucleic acid target, and wherein the capture oligonucleotide hybridizes to the reporter probe in the absence of the nucleic acid target such that plasmonic coupling electromagnetic enhancement occurs between neighboring reporter and capture nanoparticles; and detecting a color change in the presence of the target due to separation of the reporter and capture nanoparticles upon binding of the target to the capture oligonucleotide.

BRIEF DESCRIPTION OF THE DRAWINGS

The foregoing summary, as well as the following detailed description of various embodiments, is better understood when read in conjunction with the appended figures. For the purposes of illustration, there is shown in the Figures exemplary embodiments; however, the presently disclosed subject matter is not limited to the specific methods and exemplary embodiments disclosed.

FIGS. 5A-5K are schematic diagrams showing various embodiments of plasmonics-active nanoparticles of according to the present disclosure: A) Metal nanoparticle; B) Dielectric nanoparticle core covered with metal nanocap; C) Spherical metal nanoshell covering dielectric spheroid core; D) Oblate metal nanoshell covering dielectric spheroid core; E) Metal nanoparticle core covered with dielectric nanoshell; F) Metal nanoshell with protective coating layer; G) Multi layer metal nanoshells covering dielectric spheroid core; H) Multi-nanoparticle structures ; I) Metal nanocube and nanotriangle/nanoprism; J) Metal cylinder; and K) legend.

DETAILED DESCRIPTION OF THE INVENTION

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "a cell" means at least one cell and can include a number of cells.

Unless otherwise defined, all technical terms used herein have the same meaning as commonly understood by one of ordinary skill in the art to which this disclosure belongs.

The terms "plasmonics-active metal nanoparticle" and "plasmonic metal nanoparticle" and "plasmonic nanoparticle" and "metal nanoparticle" and "nanoparticle" and "NP" are herein used interchangeably.

As used herein, the term "nanostar" or "NS" means a nanoparticle which has a single core section with two or more protrusions emitting from the core section of the nanoparticle. These protrusions are usually conical or pyramidal in form, but not always.

Figure 1A:
FIGS. 1A-1D are schematic diagrams showing a plasmonics-active nanoprobe according to one or more embodiments of the present disclosure. A) Nanoparticle having probe DNA sequence and label attached at the middle of the probe DNA sequence (probe-NP) is separate from nanoparticle with complementary LNA sequence (LNA-NP). B) Nanoparticle having probe DNA sequence and label (probe-NP) is shown hybridized to nanoparticle with LNA sequence (LNA-NP) such that the label is affected by electromagnetic (EM) enhancement due to plasmonics coupling. C) In the presence of the target DNA sequence, the target DNA sequence hybridizes to the LNA sequence causing the nanoparticles to separate interfering with the plasmonics coupling such that the label is is no longer affected by electromagnetic (EM) enhancement due to plasmonics coupling. D) Legend.
Figure 1B:
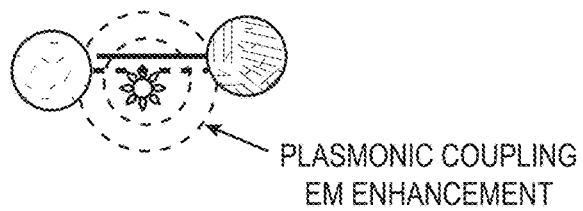
Figure 1C:
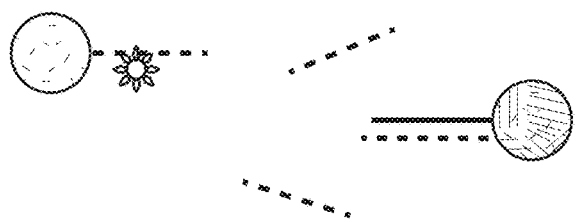
Figure 1D:
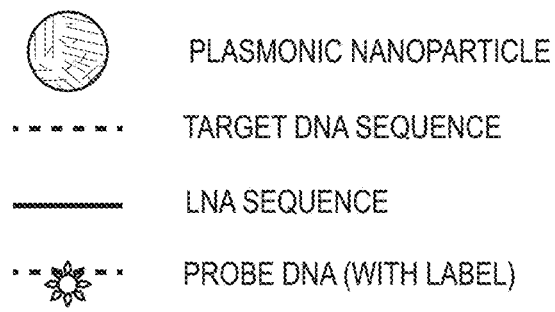

FIGS. 1A-1C are schematic diagrams showing a plasmonics-active nanoprobe according to one or more embodiments of the present disclosure. The plasmonic nanoparticles (NPs) shown in FIG. 1A can be, for example, silver or gold nanoparticles. In FIG. 1A, one NP is shown having an attached probe DNA and a separate NP has a complementary locked nucleic acid (LNA) sequence. The probe DNA has a sequence identical to the target sequence of interest and label bound in the middle portion of the sequence. The label can be a Raman dye. The label is bound in such a way that it does not sterically prevent the probe DNA from hybridization with another complementary sequence. When these two types of NPs (i.e., probe-NPs and LNA-NPs) are mixed, the DNA and LNA hybridize due to their complementary sequences. As a result the Raman label is "trapped" between the two metal nanoparticles. Due to the interparticle plasmonics coupling described above, upon excitation of the label molecule (e.g., using a laser or other appropriate energy source), the electromagnetic enhancement of the Raman signal is very intense, leading to an extremely strong SERS signal of the Raman label (FIG. 1B). However, if the target DNA of interest is introduced to the mixture at the same time as with the probe-NPs, there is a "competitive hybridization" between the target DNA and the probe-NP with the LNA-NPs. Therefore, the target DNA prevents the probe-NPs and LNA NP from being in close proximity, thus inhibiting the interparticle plasmonics coupling effect for the Raman label (FIG. 1C). As a result, upon excitation the SERS signal of the Raman label is substantially decreased. The decrease of the SERS signal intentity can be used as a parameter for monitoring and quantitatively detecting the target DNA in the assay.

While the probe is shown in FIG. 1 as probe DNA, the probe is not limited to DNA and can be another form of olionucleotide such as, for example, a RNA, a LNA, an anti-microRNA, or a siRNA. Similarly, the LNA sequence shown in FIG. 1 is not limited to LNA and can be another form of olionucleotide such as, for example, RNA or DNA. The target is a DNA sequence in FIG. 1, but is also not limited to DNA and can be an RNA, a microRNA, a mRNA, or a single polynucleotide polymorphism (SNP).

Another way of referring to the probe olionucleotide shown in FIGS. 1A-1C is as a "reporter olionucleotide" or "reporter probe". This is because the label is attached to the probe olionucleotide. Thus, the terms "probe-NP" and "reporter-NP" are herein used interchangeably for the purposes of the specification and claims. Similarly, another way of referring to the LNA olionucleotide shown in FIGS. 1A-1C is as a "capture oligonucleotide". This is because the LNA is the olionucleotide that hybridizes with the target olionucleotide. Thus, the terms "LNA-NP" and "capture-NP" are herein used interchangeably for the purposes of the specification and claims.

Figure 2A:
FIGS. 2A-2D are schematic diagrams showing a plasmonics-active nanoprobe according to FIGS. 1A-1D except that the label is attached to the probe DNA sequence at the end rather than at the middle. A) Nanoparticle having probe DNA sequence and label attached at the end of the probe DNA sequence (probe-NP) is separate from nanoparticle with complementary LNA sequence (LNA-NP). B) Nanoparticle having probe DNA sequence and label (probe-NP) is shown hybridized to nanoparticle with LNA sequence (LNA-NP) such that the label is affected by electromagnetic (EM) enhancement due to plasmonics coupling. C) In the presence of the target DNA sequence, the target DNA sequence hybridizes to the LNA sequence causing the nanoparticles to separate interfering with the plasmonics coupling such that the label is is no longer affected by electromagnetic (EM) enhancement due to plasmonics coupling. D) Legend.
Figure 2B:
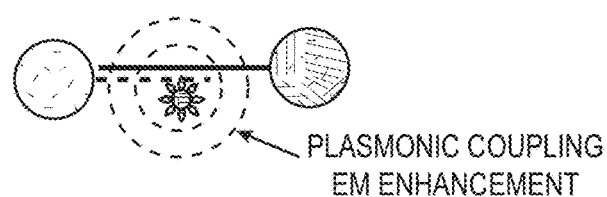
Figure 2C:
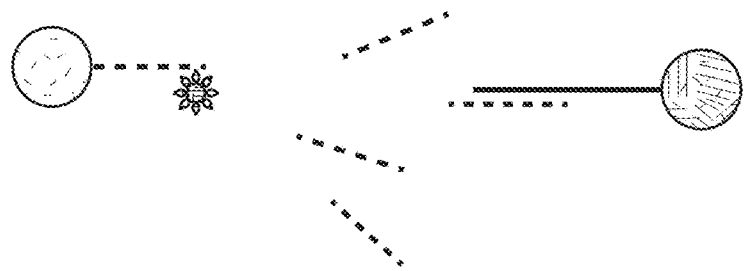
Figure 2D:
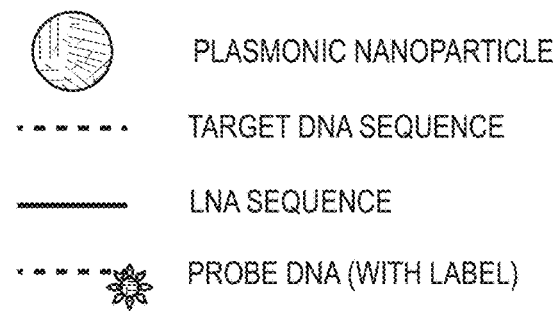

FIG. 2A-2C illustrate another embodiment of the nanoprobes and their use according to the present disclsoure. In FIG. 2A the label is positioned at the end of the DNA (not in the middle as in FIG. 1). The length of the LNA can be designed with a longer sequence such that after hybridization, the label is in the middle in between the 2 nanoparticles.

Figure 3A:
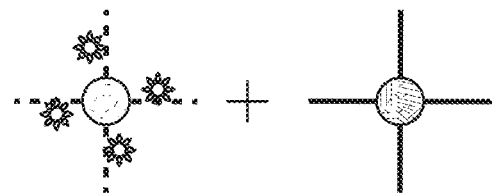
FIGS. 3A-3C are schematic diagrams showing plasmonics-active nanoprobes according to FIGS. 1A-1B forming a nano-network having strong plasmonics coupling. A) Nanoparticle having probe DNA sequence and label attached at the middle of the probe DNA sequence (probe-NP) is shown being contacted with nanoparticle with complementary LNA sequence (LNA-NP). B) Probe-NP is shown hybridized to LNA-NP such that the label is affected by electromagnetic (EM) enhancement due to plasmonics coupling. C) The hybridized nanoprobes of (B) are shown in a nano-network having strong plasmonics coupling.
Figure 3B:
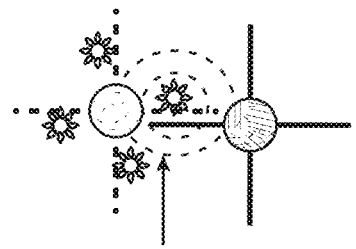
Figure 3C:
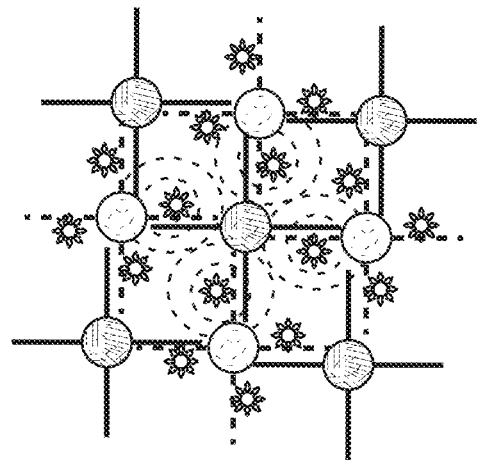

FIGS. 3A-3C show plasmonics-active nanoprobes according to FIGS. 1A-1B forming a nano-network having strong plasmonics coupling. In this situation multiple hybridizations between probe-NPs and LNA-NPs (FIG. 3B) lead to the formation of an assembly or network of nanoparticles having strong plasmonics coupling (FIG. 3C). This nano-network plasmonic coupling effect produces an extremely intense SERS signals from the Raman label molecules embedded within the NP network upon excitation (e.g., using a laser or other appropriate energy sources).

Figure 4A:
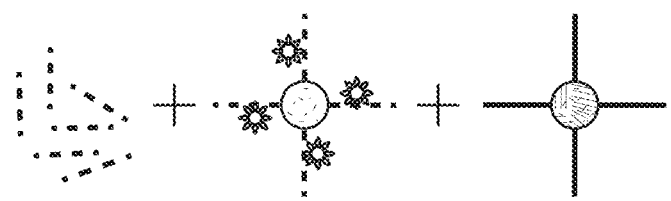
FIGS. 4A-4B are schematic diagrams showing a plasmonics-active nanoprobe according to FIG. 1C in the presence of target DNA such that hybrization of the target DNA with the LNA interferes with plasmonic coupling. A) Target DNA is contacted with probe-NP and LNA-NP. B) The target DNA hybridizes to the LNA sequence causing the nanoparticles to separate interfering with the plasmonics coupling such that the label is is no longer affected by electromagnetic (EM) enhancement due to plasmonics coupling.
Figure 4B:
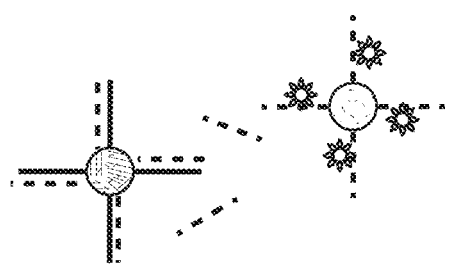

As shown in FIG. 4, if the target DNA of interest is introduced to the mixture at the same time as the probe-NPs and LNA-NPs (FIG. 4A), there is a "competitive hybridization" between the target DNA and the probe-NP with the LNA-NP (FIG. 4B). Therefore, the target DNA prevents the probe-NPs and LNA NP from be in close proximity, thus inhibiting the interparticle plasmonics coupling effect for the Raman label. As a result, the SERS signal of the Raman label is substantially decreased.

Plasmon resonances arise within a metallic nanoparticle from the collective oscillation of free electrons driven by an incident optical field. The plasmonic response of nanoparticles have played a role in a growing number of applications, including surface-enhanced Raman scattering (SERS), chemical sensing, drug delivery, photothermal cancer therapy and new photonic devices. SERS technologies are being developed for applications in chemical sensing, biological analysis and medical diagnostics. The nanoprobes of the present disclosure can include nanoparticles and semi-nanoshells consisting of a layer of nanoparticles coated by silver on one side (nanocaps or half-shells).

Several groups have shown that plasmon resonances of spherical shells can be tuned by controlling the shell thickness [M. M. Kerker, *Acc. Chem. Res.*, 17, 370 (1984); J. B. Jackson, S. L. Westcott, L. R. Hirsch, J. L. West and N. H. Halas, "*Controlling the surface enhanced Raman effect via the nanoshell geometry,*" *Appl. Phys. Lett.*, vol. 82, 257-259, 2003]. These shells consist typically of a metallic layer over a dielectric core. In the present disclosure, the analysis was extended to spheroidal shells and demonstrates how plasmon resonances (both longitudinal and transverse modes) can be influenced by both shell thickness and aspect ratio.

A number of researchers have examined the plasmonic response of the solid spheroidal particle in their analysis of surface-enhanced Raman scattering, although the spheroidal shell appears not to have been investigated. Prolate and oblate spheroidal shells have been investigated and show some interesting qualitative features in their plasmon resonances. The results indicate that the spheroidal shell presents two degrees of freedom for tuning: the shell thickness and the shell aspect ratio [S. J. Norton and T. Vo-Dinh, *"Plasmonic Resonances of Nanoshells of Spheroidal Shape"*, IEEE Trans. Nanotechnology, 6, 627-638 (2007)]. Recently it has been shown that nanostar-shaped structures can also be plasmonics-active and induce strong SERS signals.

FIGS. 5A-5J are schematic diagrams showing various embodiments of plasmonics-active nanoparticles of according to the present disclosure: A) Metal nanoparticle; B) Dielectric nanoparticle core covered with metal nanocap; C) Spherical metal nanoshell covering dielectric spheroid core; D) Oblate metal nanoshell covering dielectric spheroid core; E) Metal nanoparticle core covered with dielectric nanoshell; F) Metal nanoshell with protective coating layer; G) Multi layer metal nanoshells covering dielectric spheroid core; H) Multi-nanoparticle structures ; I) Metal nanocube and nanotriangle/nanoprism; and J) Metal cylinder.

Figure 6:
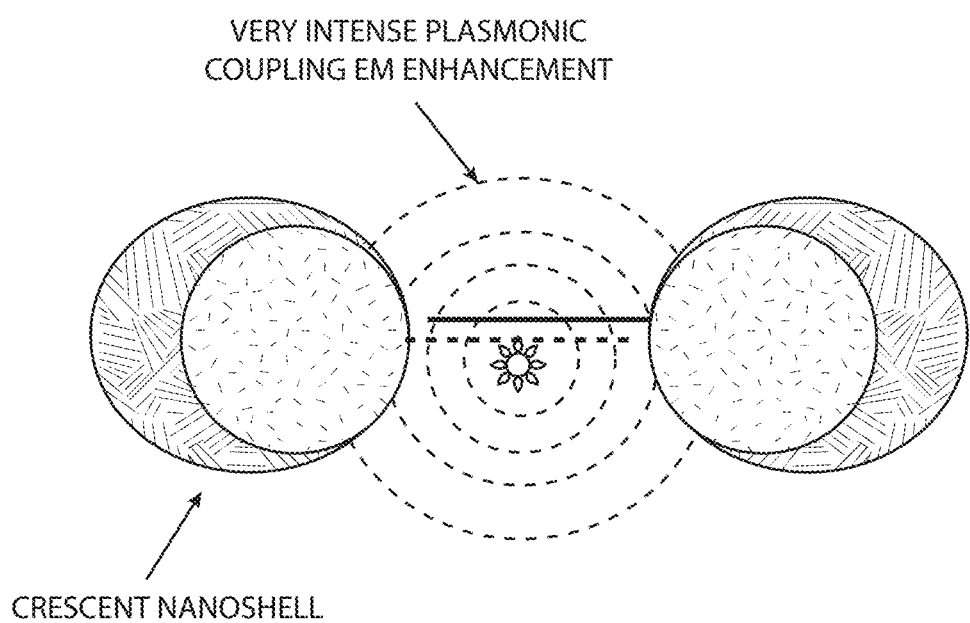
FIG. 6 is a schematic diagram showing the enhanced plasmonic coupling in crescent metal nanoparticles according to FIG. 5B.

FIG. 6 shows an embodiment where the plasmonics NPs have a "crescent structure" partially covering a dielectric core (e.g., silica, polymeric material, etc.). The side of the crescent end produce extremely strong plasmonics enhancement. Furthermore the plasmonic coupling between these crescent-induced enhancements can produce a combined very strong NPCI effect.

The nanoprobes of the present disclosure can be prepared using either silver (or gold) nanoparticle colloids. Gold nanoshells can be fabricated using published methods using a mechanism involving nucleation and then successive growth of gold nanoparticles around a silica dielectric core. In addition, the nanoprobes can include use of nanospheres spin-coated on a solid support in order to produce and control the desired roughness. The nanostructured support can be subsequently covered with a layer of silver that provides the conduction electrons required for the surface plasmon mechanisms. Among the techniques based on solid substrates, the methods can include using simple nanomaterials, such as Teflon or latex nanospheres. Teflon and latex nanospheres are commercially available in a wide variety of sizes. The shapes of these materials are very regular and their size can be selected for optimal enhancement. These materials can consist of isolated dielectric nanospheres (30-nm diameter) coated with silver producing systems of half-nano shells, referred to as nanocaps. The nanocaps can be 300-nm diameter polymer nanospheres covered by a 100-nm thick silver nanocap (half-nanoshell) coating. The nanoparticles can be sonicated to release them from the underlying substrate. The effect of the sphere size and metal layer thickness upon the SERS effect can be easily investigated. By rotating the platform supporting the nanospheres, one can extend the solver coverage and produce the "crescent structures" shown in FIG. 10. The silver coated nanospheres were found to be among the most plasmonics-active investigated. Gold can also be used instead of silver to coat over nanoparticle materials.

Known methods can be employed to immobilize the bioreceptors to metal nanoparticles to prepare the nanoprobes of the present disclosure. By "bioreceptor" is meant the nucleic acid stem of the iMS nanoprobes of the present disclosure as well as the "bioreceptor" on the nanoprobes for detecting proteins shown in FIGS. 7 and 8 that can be amino acid based. The immobilization of biomolecules (such as, e.g., DNA, RNA, LNA, proteins, antibodies, etc.) to a solid support can use a wide variety of methods published in the literature. Binding can be performed through covalent bonds usually takes advantage of reactive groups such as amine ($-NH_2$) or sulfide ($-SH$) that naturally are present or can be incorporated into the biomolecule structure. Amines can react with carboxylic acid or ester moieties in high yield to form stable amide bonds. Thiols can participate in maleimide coupling, yielding stable dialkylsulfides.

A solid support of interest is gold (or silver) nanoparticles. The majority of immobilization schemes involving Au (Ag) surfaces utilize a prior derivatization of the surface with alkylthiols, forming stable linkages. Alkylthiols readily form self-assembled monolayers (SAM) onto silver surfaces in micromolar concentrations. The terminus of the alkylthiol chain can be used to bind biomolecules, or can be easily modified to do so. The length of the alkylthiol chain has been found to be an important parameter, keeping the biomolecules away from the surface. Furthermore, to avoid direct, non-specific DNA adsorption onto the surface, alkylthiols can be used to block further access to the surface, allowing only covalent immobilization through the linker [Steel, A. B.; Herne, T. M.; Tarlov, M. J. Anal. Chem. 1998, 70, 4670-7; Herne, T. M.; Tarlov, M. J. J. Am. Chem. Soc. 1997, 119, 8916-20].

Silver surfaces have been found to exhibit controlled self-assembly kinetics when exposed to dilute ethanolic solutions of alkylthiols. The tilt angle formed between the surface and the hydrocarbon tail ranges from 0 to 15°. There is also a larger thiol packing density on silver, when compared to gold [Burges, J. D.; Hawkridge, F. M. Langmuir 1997, 13, 3781-6]. After SAM formation on gold/silver nanoparticles, alkylthiols can be covalently coupled to biomolecules. The majority of synthetic techniques for the covalent immobilization of biomolecules utilize free amine groups of a polypeptide (enzymes, antibodies, antigens, etc) or of amino-labeled DNA strands, to react with a carboxylic acid moiety forming amide bonds. As a general rule, a more active intermediate (labile ester) is first formed with the carboxylic acid moiety and in a later stage reacted with the free amine, increasing the coupling yield. Successful coupling procedures include:

Binding Procedure Using N-hydroxysuccinimide (NHS) and its derivatives. The coupling approach involves the esterification under mild conditions of a carboxylic acid with a labile group, an N-hydroxysuccinimide (NHS) derivative, and further reaction with free amine groups in a polypeptide (enzymes, antibodies, antigens, etc) or amine-labeled DNA, producing a stable amide [Boncheva, M.; Scheibler, L.; Lincoln, P.; Vogel, H.; Akerman, B. Langmuir 1999, 15, 4317-20]. NHS reacts almost exclusively with primary amine groups. Covalent immobilization can be achieved in as little as 30 minutes. Since $H_2O$ competes with $-NH_2$ in reactions involving these very labile esters, it is important to consider the hydrolysis kinetics of the available esters used in this type of coupling. The derivative of NHS O—(N-succinimidyl)-N,N,N',N'-tetramethyluronium tetrafluoroborate, increase the coupling yield by utilizing a leaving group that is converted to urea during the carboxylic acid activation, hence favorably increasing the negative enthalpy of the reaction.

Binding Procedure Using Maleimide. Maleimide can be used to immobilize biomolecules through available $-SH$ moieties. Coupling schemes with maleimide have been proven useful for the site-specific immobilization of antibodies, Fab fragments, peptides, and SH-modified DNA strands. Sample preparation for the maleimide coupling of a protein involves the simple reduction of disulfide bonds between two cysteine residues with a mild reducing agent, such as dithiothreitol, 2-mercaptoethanol or tris(2-carboxyethyl)phosphine hydrochloride. However, disulfide reduction will usually lead to the protein losing its natural conformation, and might impair enzymatic activity or antibody recognition. The modification of primary amine groups with 2-iminothiolane hydrochloride (Traut's reagent) to introduce sulfydryl groups is an alternative for biomolecules lacking them. Free sulfhydryls are immobilized to the maleimide surface by an addition reaction to unsaturated carbon-carbon bonds [Jordan, C. E., et al., 1997].

Binding Procedure Using Carbodiimide. Surfaces modified with mercaptoalkyldiols can be activated with 1,1'-carbonyldiimidazole (CDI) to form a carbonylimidazole intermediate. A biomolecule with an available amine group displaces the imidazole to form a carbamate linkage to the alkylthiol tethered to the surface [Potyrailo, R. A., et al., 1998].

As described herein above, the efficacy of the nanoprobes disclosed herein is demonstrated for SERS-based DNA Detection. In the approach provided herein, nanoparticles are coupled using the shortest separation distance in order to induce the strongest possible plasmonics coupling and a maximum SERS enhancement. Previous studies have shown that nanoparticles can be coupled using DNA oligonucleotides with over 8 bases. The use of DNA oligonucleotides shorter than 8 bases in plasmonic coupling-based DNA detection had not been demonstrated. The main reason may be due to the thermal instability of short DNA-DNA duplexes. To overcome this barrier, short locked nucleic acids (LNAs) having 7 bases can be utilized in the present nanoprobe compositions in order to couple nanoparticles in a separation distance between 2 to 3 nm, because LNAs can offer a higher thermal stability and melting temperature for LNA-DNA duplexes [Ref: F. McKenzie, K. Faulds, D. Graham, "*LNA functionalized gold nanoparticles as probes for double stranded DNA through triplex formation, Chem. Commun.* 2008, 267-2369]. Procedures for reversible switching of DNA-gold nanoparticles have been described [P. Harazika, B. Ceyhan; C M Niemeyer, Andew. *Chem. International*, 43, 6469-71, 2004].

In the methods of the present disclosure, 30-nm-diameter silver NPs can be first functionalized with 0.5-µM dithiolated LNAs with the sequence of 5'-dithiol-GGGCGGG-3' (referred to as LNA-NPs) or the complementary DNA probes with the sequence of 3'-CCCGCCC-dithiol-5' (referred to as Probe-NPs) (see FIGS. 1A-1C). The DNA probes can be internally labeled with a Raman dye, Cy3, as the signal reporter located in the middle of the probe DNA sequence. These functionalized NPs can then be further conjugated with low molecular weight thiolated poly(ethylene glycol)s (HS-PEGs). These short PEGs were found to provide the silver NPs stability buffer solution [Ximei Qian, Xi Zhou and Shuming Nie "*Surface-Enhanced Raman Nanoparticle Beacons Based on Bioconjugated Gold Nanocrystals and Long Range Plasmonic Coupling*" JACS (2008) 130: 14934-14935]. To displace the potential non-specifically adsorbed LNAs or DNAs, 6-Mercapto-1-hexanol (MCH) can be used in the final step to passivate the silver surface.

To induce a plasmonic coupling effect, LNA-NPs and Probe-NPs can be mixed in a volume ratio of 1:1 in order to form LNA-Probe DNA duplexes (FIGS. 3A-3B). The mixture can be allowed to react at room temperature in a 10-mM sodium phosphate buffer solution (pH 7.0) containing 50 mM NaCl and 2 mM $MgCl_2$. The duplex formation assembles nanoparticles into a three-dimensional nano-network of NPs having the Raman dye Cy3 located between two adjacent NPs (FIG. 3C), thus resulting in a strong plasmonic coupling effect, leading to an increased SERS signal of the Raman labels. FIGS. 4A-4B depict the mechanism for the detection of particular DNA sequences (target DNA). In this approach, the sequence of probe DNA is designed to have the same sequence as the target DNA. Therefore, the target DNA strands are then used as compettitors of probe DNA in a compettitve binding process. As a result, the DNA target interferes with the plasmonic coupling effect by competing with Probe-NPs for binding to LNA-NPs. As a result, the SERS signal due the plasmonics coupling is quenched.

Figure 7A:
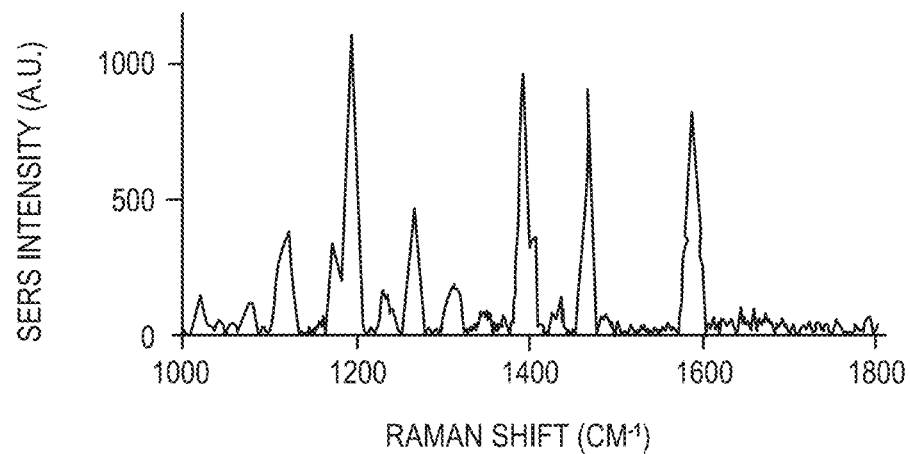
FIGS. 7A-7B are SERS spectra of Cy3 Raman peaks of the nanoprobes having Cy3 as the label in the presence and absence of target DNA according to embodiments of the present disclosure. A) SERS spectra of Cy3 Raman peaks for a mixture of reporter-NP and capture-NP nanoprobes in the absence of target DNA. B) SERS spectra of Cy3 Raman peaks for a mixture of reporter-NP and capture-NP nanoprobes in the presence of 1 µM target DNA strands showing the absence of the Cy3 Raman peaks.
Figure 7B:
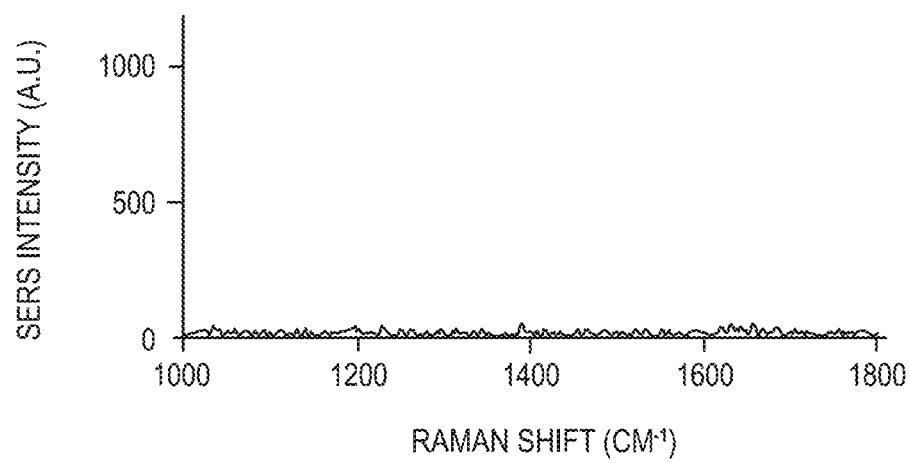

FIGS. 7A-7B show the increased SERS intensity of the Cy3 Raman peaks in the presence of both LNA-NPs and probe-NPs (FIG. 7A) as compared to the SERS intensity of probe-NPs in the absence of LNA-NPs (FIG. 7B). The enhanced SERS signal indicates that plasmonic coupling was induced by the hybridization reaction between the LNA and probe oligonucleotides. In addition, a dramatic color change can be observed over the course of 20 minutes when the probe-NP and LNA-NP nanoprobes were contacted with the target.

To demonstrate the detection of DNA with the nanoprobes of the present disclosure, probe-NPs and target DNA strands (1 µM) were mixed prior to addition of a solution of LNA-NPs in order to ensure that the DNA probes and target DNA can react with LNA oligonucleotides at the same time. After adding LNA-NPs, the mixture was allowed to react for 20 min at room temperature and immediately followed by SERS measurements. FIG. 7B shows the quenched SERS signal in the presence of target DNA strands in the mixture of LNA-NPs and probe-NPs indicating that plasmonic coupling effect was interfered with by the formation of LNA-target DNA duplexes.

Figure 8:
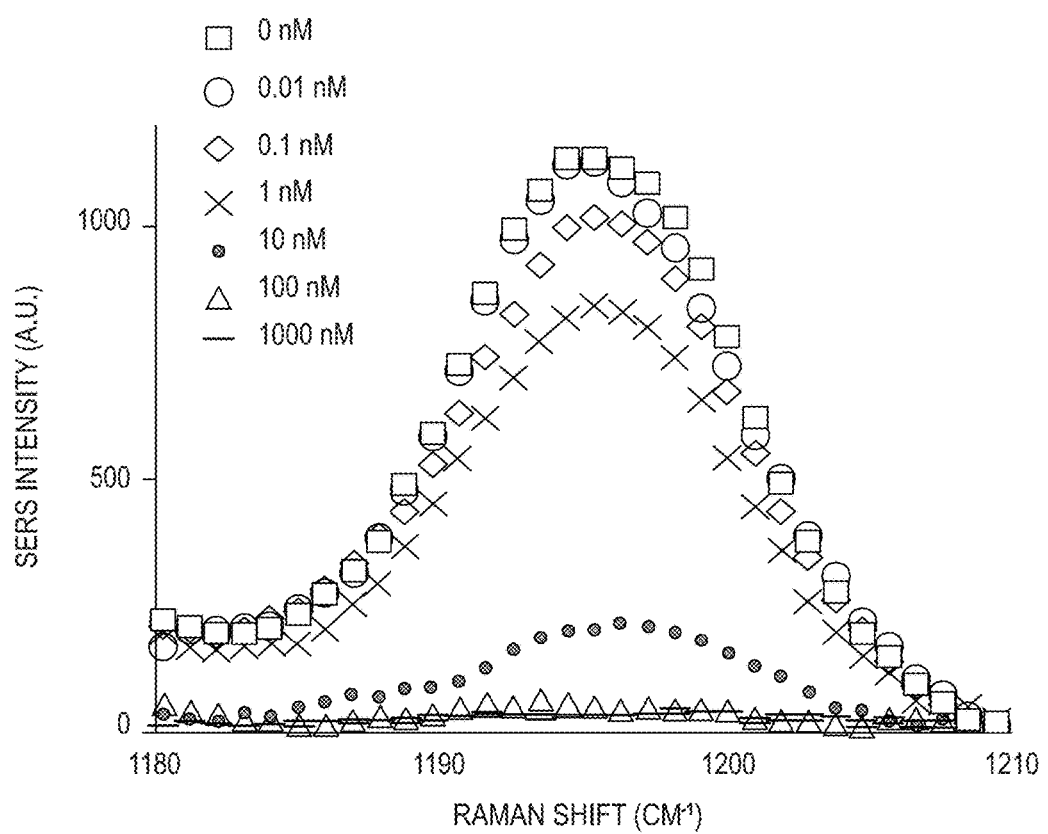
FIG. 8 is a graph showing a series of SERS spectra of a mixture of the nanoprobes (reporter-NPs and capture-NPs) with Cy3 as the label showing the major Raman peak of the Cy3 label at 1195 cm$^{-1}$ with varying concentrations of target DNA strands from 0 to 1 µm. The concentrations of reporter-NP and capture-NP were kept constant.

The quantitative properties of the nanoprobes of the present disclosure are shown in FIG. 8. The concentrations of the LNA-NPs and probe-NPs were held constant and the concentration of target DNA was varied from 0 to 1 µM. FIG. 8 shows that the SERS intensity of probe-NPs at 1195 $c^{m-1}$ decreased with increasing target DNA concentration, indicating that plasmonic coupling between LNA-NPs and Probe-NPs was differentially interfered with in the presence of various concentrations of target DNA. The minimum target DNA concentration which can cause detectable interference in the current system can be about 100 pM. The results of this study demonstrate the usefulness of this technique for quantitative DNA diagnostics.

The nanoprobe compositions and methods of the present disclosure provide a new approach for SERS-based DNA detection through interference with the plasmonic coupling effect in metal nanoparticle-networks. LNAs can offer the capability to couple nanoparticles with a very short separation distance (2~3 nm) with high thermal stability. The highly specific and narrow Raman spectral bands can allow multiple assays to be performed simultaneously in a single sample solution without washing steps when using multiple Raman labels.

One of the advantages of Raman/SERS is the ability for multiplex detection. Employment of the SERS technique permits the use of many different probe molecules, allowing the narrow band spectral characteristics of Raman-based probes to be used to advantage for sensitive, specific analysis of microarrays. Multiple probes, each designed to detect a specific DNA target can be used and detected simultaneously using a multiplex detection system as described herein.

Figures 9A, 9B:
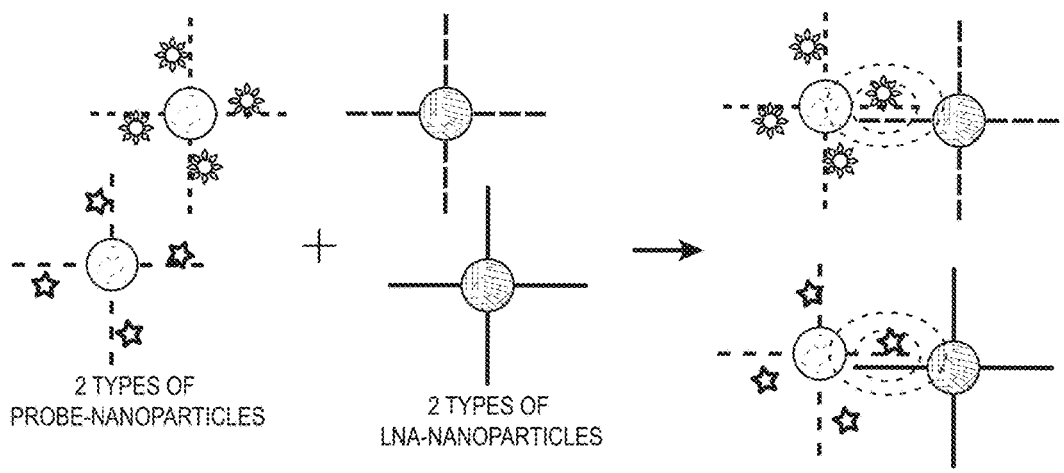
FIGS. 9A-9B are schematice diagrams of the nanoprobes according to FIGS. 3A-3B, except that in this case two types of probe-NP and LNA-NP pairs are shown, each directed to a separate target (i.e., the two separate probe- and LNA-NPs have different probes, labels and LNAs), allowing for the use of multiplex NPCI detection to simultaneously detect more than one target DNA in a solution through detection of plasmonic coupling interference due to selective separation of complementary probe-NP and LNA-NP in the presence of each target. A) The two types of probe-NP and LNA-NP pairs having different probes (depicted as black or grey broken lines), labels (depicted as solid or open stars) and LNAs (depicted as black or grey lines) are shown being contacted together. B) The two types of probe-NP and LNA-NP pairs are shown selectively hybridized together.

FIGS. 9A-9B are schematice diagrams showing the nanoprobes according to FIGS. 3A-3B, except that in this case two types of probe-NP and LNA-NP pairs are shown, each directed to a separate target (i.e., the two separate probe- and LNA-NPs have different probes, labels and LNAs). This allows for the use of multiplex NPCI detection to simultaneously detect more than one target DNA in a solution through detection of plasmonic coupling interference due to selective separation of complementary probe-NP and LNA-NP in the presence of each target. In FIG. 9A the two types of probe-NP and LNA-NP pairs having different probes (depicted as black or grey broken lines), labels (depicted as solid or open stars) and LNAs (depicted as black or grey lines) are shown being contacted together. In FIG. 9B the two types of probe-NP and LNA-NP pairs are shown selectively hybridized together.

Figures 10A, 10B:
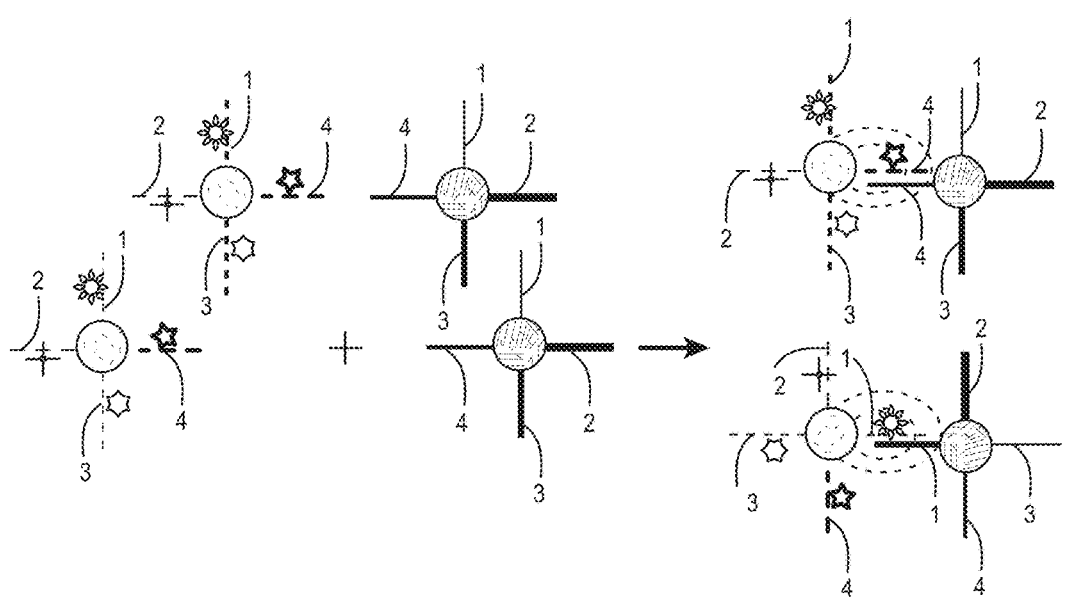
FIGS. 10A-10B are schematic diagrams of the nanoprobes according to FIGS. 3A-3B, except that in this case a single pair of probe-NPs and LNA-NPs is shown directed to four different targets, each probe-NP molecule and LNA-NP molecule having four different probes, labels and LNAs, allowing for the use of multiplex NPCI detection to simultaneously detect the four target DNAs in a solution through detection of plasmonic coupling interference due to selective separation of complementary probe-NP and LNA-NP in the presence of each target. A) The probe-NP molecules and LNA-NP molecules are shown being contacted together. The four different probes are depicted as black broken line, lighest grey broken line, medium grey dashed line or darkest grey dashed line, the four different labels are depicted as solid or open stars having different numbers of points, and the four different LNAs are depicted as black unbroken line, lighest grey unbroken line, medium grey unbroken line or darkest grey unbroken line. B) The probe-NP and LNA-NP molecules are shown selectively hybridized together.

FIGS. 10A-10B are schematic diagrams of the nanoprobes according to FIGS. 3A-3B, except that in this case a single pair of probe-NPs and LNA-NPs is shown directed to four different targets, each probe-NP molecule and LNA-NP molecule having four different probes, labels and LNAs, allowing for the use of multiplex NPCI detection to simultaneously detect the four target DNAs in a solution through detection of plasmonic coupling interference due to selective separation of complementary probe-NP and LNA-NP in the presence of each target. In FIG. 10A the probe-NP molecules and LNA-NP molecules are shown being contacted together. The four different probes are depicted as black broken line, lighest grey broken line, medium grey dashed line or darkest grey dashed line, the four different labels are depicted as solid or open stars having different numbers of points, and the four different LNAs are depicted as black unbroken line, lighest grey unbroken line, medium grey unbroken line or darkest grey unbroken line. In FIG. 10B the probe-NP and LNA-NP molecules are shown selectively hybridized together.

Figures 11A, 11B:
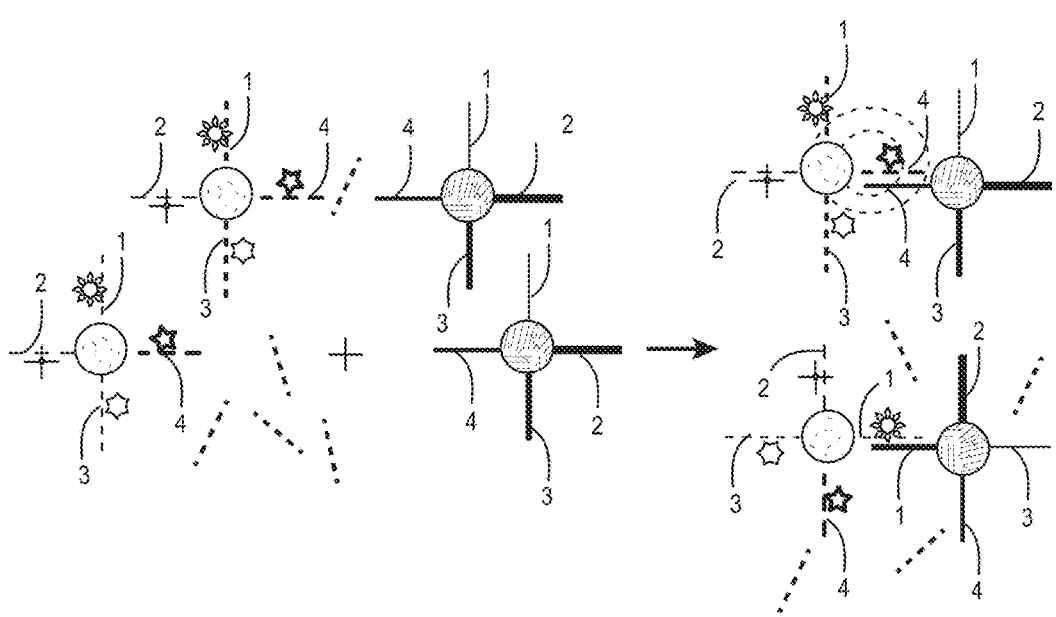
FIGS. 11A-11B are schematice diagrams of the nanoprobes according to FIGS. 10A-10B, except that in this case the probe-NPs and LNA-NPs are shown in the presence of one of four target DNAs. A) The probe-NP molecules and LNA-NP molecules are shown being contacted together in the presence of target DNA. The four different probes are depicted as black broken line, lighest grey broken line, medium grey dashed line or darkest grey dashed line, the four different labels are depicted as solid or open stars having different numbers of points, and the four different LNAs are depicted as black unbroken line, lighest grey unbroken line, medium grey unbroken line or darkest grey unbroken line. The target DNA is shown depicted as medium grey dashed line. B) The presence of the specific target DNA sequence (depicted as medium grey dashed line) only interferes with the plasmonic coupling affecting the label attached to the probe directed to that specific target DNA. The signal originated from the other three labels remain unchanged since the network plasmonic coupling is not interfered with in the absence of the three remaining target DNAs. Note that the plasmonic coupling that is not interfered with is only shown for one of the three remaining probes with attached label.

FIGS. 11A-11B are schematice diagrams of the nanoprobes according to FIGS. 10A-10B, except that in this case the probe-NPs and LNA-NPs are shown in the presence of one of four target DNAs. In FIG. 11A the probe-NP molecules and LNA-NP molecules are shown being contacted together in the presence of target DNA. The four different probes are depicted as black broken line, lighest grey broken line, medium grey dashed line or darkest grey dashed line, the four different labels are depicted as solid or open stars having different numbers of points, and the four different LNAs are depicted as black unbroken line, lighest grey unbroken line, medium grey unbroken line or darkest grey unbroken line. The target DNA is shown depicted as medium grey dashed line. In FIG. 11B the presence of the specific target DNA sequence (depicted as medium grey dashed line) only interferes with the plasmonic coupling affecting the label attached to the probe directed to that specific target DNA. The signal originated from the other three labels remain unchanged since the network plasmonic coupling is not interfered with in the absence of the three remaining target DNAs. Note that in FIG. 11 the plasmonic coupling that is not interfered with is only shown for one of the three remaining probes with attached label.

Figure 12:
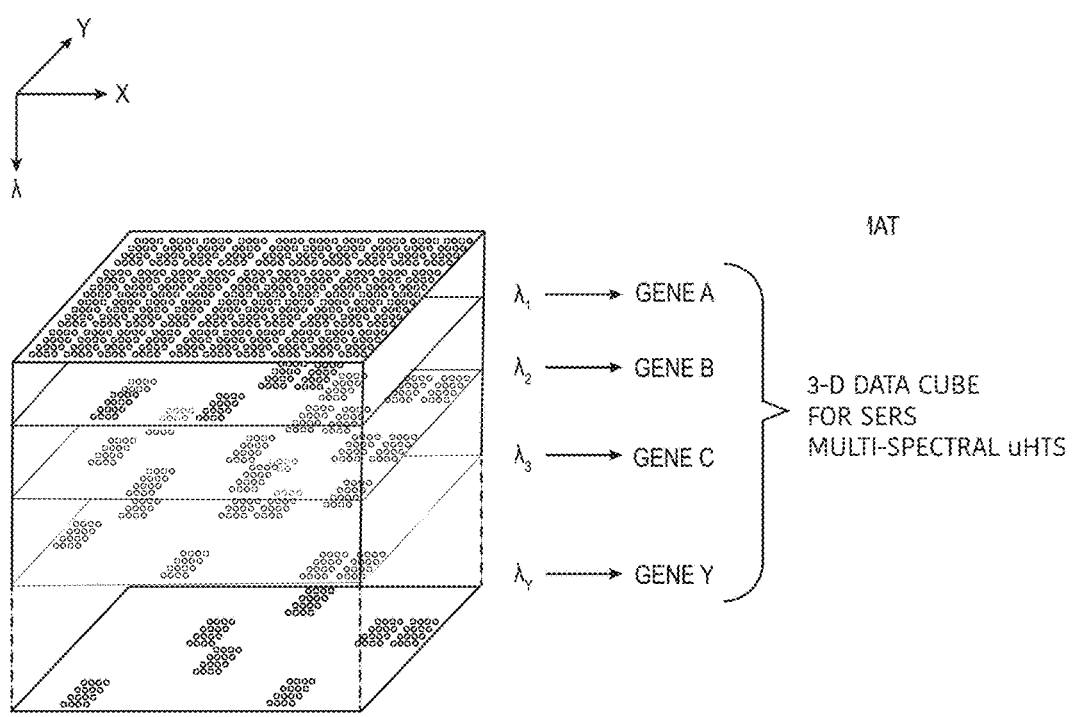
FIG. 12 is a schematic diagram showing a Raman data cube in multi-spectral imaging of a microarray for multiplex NPCI detection to simultaneously detect more than one target DNA in a solution according to embodiments of the present disclosure.

Raman spectroscopy can be used as a modality for detection in ultra-high throughput microarray systems. Using a multispectral Raman imaging system, the entire emission spectrum of multiple wavelengths (~10-100) can be collected on the entire image in the field of view. The resulting multispectral image can be presented as a 3-D data cube as shown in FIG. 12, consisting of two spatial dimensions (x, y) defining the image area of interest as well as wavelength ($\lambda$), as the third dimension indicated in the FIG. 12 on the Z axis.

Multiplex capability, which allows for monitoring of a large number of molecular processes simultaneously, is an important feature in systems biology research. A wide variety of luminescence labels (e.g., fluorescent labels, chemiluminescent labels, quantum dots, etc.) have previously been developed for bioassays. Although detection sensitivities achieved by luminescence techniques are adequate, the spectral overlap of the relatively large bandwidth of fluorescence spectra limit the number of labels that can be used simultaneously. Therefore, alternative techniques with improved multiplex capability are needed. Due to the narrow bandwidths of Raman bands, the multiplex capability of the SERS probes of the present disclosure is excellent in comparison to the other spectroscopic alternatives.

For comparison purposes, consider the detection of crystal fast violet (CFV) dye in fluorescence and SERS. The spectral bandwidth of CFV label in the fluorescence spectrum is relatively broad (approximately 50-60 nm halfwidth), whereas the bandwidth of the SERS spectrum of the same CFV label is much narrower (<0.5 nm or 3 cm$^{-1}$ halfwidth) (data note shown). In another example of the SERS advantage in "label multiplexing", HIV and Hepatitis C (HCV) gene sequences were simultaneously detected by acquiring SERS spectra of a mixture of a CFV-labeled HIV gene sequence and a BCB-labeled HCV gene sequence (data not shown). These results demonstrate the advantage of SERS as a practical tool for the identification and differentiation of multiple genes or gene expression in diagnostics or HTS applications.

The data also indicate that use of SERS can increase the multiplexing capability over currently used luminescence techniques by a factor of several orders of magnitude. In a typical Raman spectrum, a spectral interval of 3000 cm$^{-1}$ can provide 3000/3 or 10$^3$ available individual spectral "intervals" at any given time. Even when allowing a deduction factor of 10 due to possible spectral overlaps, it should be possible to find 100 labels that can be used for labeling multiple probes simultaneously. This multiplex advantage is particularly useful in ultra-high-throughput analyses where multiple gene targets can be screened in a highly parallel multiplex modality. For example, a 10,000 (10$^4$) microarray can be labeled-multiplexed with 10-100 labels to provide a 3-D data cube of 10$^5$-10$^6$ (one million) data.

A multiplex NPCI system primarily consists of an AOTF, an excitation laser, a long pass filter, and a detector. The basic system can be used to acquire images of samples at different wavelengths. To perform high throughput measurements, the RMS system can be coupled to an imaging optical system. A personal computer can be used to control a CCD, scan the RF signal applied to the AOTF, and perform data acquisition. The light emitted from the microarray platform can be collected by an imaging system, filtered by the AOTF, and then imaged onto a CCD. By changing the wavelength of the AOTF, a spectrum can be acquired as a series of images (one for each wavelength).

A TeO$_2$ AOTF purchased from Brimrose Corporation, Baltimore, Md. (model TEAF 10-45-70-S) can be used. According to the manufacturer, the AOTF has an effective wavelength range of 450 nm to 700 nm (corresponding drive frequency 178-100 MHz). For visible wavelengths in a tellurium oxide crystal, the applied acoustic wave is RF and can be switched very quickly compared to other technologies. Unlike a liquid crystal tunable filter where the bandwidth is fixed by the design and construction, an AOTF can vary the bandwidth by using closely spaced RF simultaneously. The spectral resolution given by the manufacturer for the AOTF used in this study was 4 nm at 633 nm. The diffraction efficiency is relatively high, typically about 70% at 600 nm. The optical aperture is 10 by 10 mm and the acceptance angle is greater than 30°. The drive power range was 1.0 to 1.5 W. The RF generator used (Brimrose-model AT) could apply 0 to 10 W of RF power and is controlled by a DOS-based computer using a 16-bit computer controller board supplied by Brimrose.

The 2-D detection system uses an intensified CCD (Andor or Roper Scientific). The interface to the PC-compatible computer is accomplished via an RS232 system. The excitation source is a HeNe or a suitable diode laser. A CCD image of the emitted SERS is acquired and can serve as a map of gene expression (concentrations and distribution). By varying the bandpass of the AOTF, images can be acquired rapidly at selected wavelengths, enabling different gene expression to be screened. The 2-D detector is oriented 5.5° from the optical axis of the AOTF (due to the diffraction angle of the AOTF at a central wavelength: 550 nm). The AOTF is placed 30-cm from the 2D-detector to allow the separation of both the diffracted and reflection images and an iris will be placed in the optical path to block to undiffracted light. A long-pass filter can be placed flush against the iris to reject any remaining laser light that may have been scattered in the process of illumination. A glass lens (5 cm diameter) is used to collect the light and form an image on the CCD. The output end of the microarray platform is placed in the object plane of the lens. The lens systems is chosen to give a total magnification to match the 2-D detector.

Another advantage of the nanoprobes of the present disclosure is that they can be used for rapid in vitro diagnostics. For example, the color of a solution containing a nanoprobe of the present disclosure can change rapidly and visibly in the presense of the target of interest. As a result, the nanoprobes of the present disclosure can be used for rapid, simple and inexpensive detection. Such a test is appropriate for environmental sensing (e.g., detecting E coli in waste streams) and global health (e.g., detecting infectious diseases) in underserved regions where access to sophisticated diagnostics facilities are not possible.

The nanosensors of the present disclosure can be used for in vivo diagnostics. The nanoprobes can be used in this manner as a real time, permanent and continuous 'health monitor'. For example, the nanoprobes can be given to a person by injection using various methodologies including: 1) deposition under the skin to form a 'smart mole' that can monitor a target in tissue or in the blood stream; 2) nanoprobes having magnetic cores can be moved to and concentrated in an area suitable for detection; and 3) the nanoprobes can be attached to a biocompatible material inside the skin layer.

In one example the nanoprobes can be injected as a colloidal solution in which the nanoprobes are polymer-coated. The nanoprobes can be embedded into a NIPAM hydrogel implant. The implant can be placed immediately under the skin to allow for optical detection in situ. The porosity of the hydrogel allows for passage of the target, while excluding larger interfering molecules. In another example, the nanoparticles of the nanoprobes can be iron oxide-gold/silver core-shell particles and the nanoprobes can be embedded in a NIPAM shell. The superparamagnetic iron oxide core can be used to concentrate the nanoprobes at a specific location in the body with a wearable magnet. Concentration of the nanoprobes at the skin surface allows for optical interrogation through the skin.

In one embodiment, the nanoprobes can be used to detect the host response to various pathogens. Both the pathogenic nucleic acids as well as the host response can be detected. The detection can be performed in the cytosol of dermal cells. Nanoprobes can be designed for detection of the human radical S-adenosyl methionine domain containing 2 (RSAD2) gene, which is involved in antiviral defense and is one of the most highly induced genes upon interferon stimulation or infection with various viruses, including human cytomegalovirus (HCMV), influenza virus, hepatitis C virus (HCV), dengue virus, alphaviruses, and retroviuses such as human immunodeficiency virus (HIV). The RSAD2 gene has emerged as a host-response biomarker for diagnosis of respiratory infections. In addition, nanosensors of the present disclosure can be prepared to detect critical pathogen biomarkers such as rfbE, fliC and mobA genes for *Escherichia coli* (*E. coli*) serotype O157:H7; mecA and femA genes for *Staphylococcus aureus* and *Staphylococcus epidermidis*; aroQ and 16S rRNA genes for *Erwinia* herbicola; protective antigen (PA) and anthrax toxin activator (atxA) genes for *Bacillus anthracis*.

Several diagnostics systems can be utilized, depending on the degree of miniaturization. For example, detection of the target can be performed using a portable Raman diagnostic system having excitation light source and an optical detector. An alternative diagnostic system can include a pocket-sized (or palm-sized) battery-operated Raman diagnostics system that is linked to the 'smart mole' by fiberoptics excitation and detection. The pocket-sized system can be operated remotely by an iPhone or similar device. Further miniaturization can shrink the size of the portable diagnostic system into the size of a 'wristwatch-sized' battery-operated Raman diagnostics device.

The nanoprobes and methods of use of the present disclosure are useful for a wide variety of applications based on DNA/RNA/protein detection including, but not limited to: biomedical applications, point-of-care diagnostics, food safety, environmental monitoring, industrial process sensing, quality control applications, biotechnology industrial control, quality control, global health, cancer research, heart disease diagnostics, homeland defense.

In addition to Raman and SERS, other photonic techniques can be used for excitation of the nanoprobes in the methods of the present disclosure. For example, other parts of the electromagnetic spectrum can be used for excitation, ranging from gamma rays and X rays throughout ultraviolet, visible, infrared, microwave and radio frequency energy.

In one embodiment, a pair of nanoprobes is provided for detecting nucleic acid targets, the pair comprising a reporter nanoprobe and a capture nanoprobe, wherein the reporter nanoprobe comprises: at least one plasmonic nanoparticle; and an oligonucleotide reporter probe attached at one end to the nanoparticle, the reporter probe having an attached optical label, and wherein the capture nanoprobe comprises: at least one plasmonic nanoparticle; and a capture oligonucleotide attached at one end to the nanoparticle, wherein the capture oligonucleotide is complementary to both the reporter probe and the nucleic acid target, and wherein the capture oligonucleotide hybridizes to the reporter probe in the absence of the nucleic acid target such that plasmonic coupling electromagnetic enhancement occurs between neighboring reporter and capture nanoparticles.

In one embodiment, a method is provided for detecting nucleic acid targets, comprising: incubating a reporter nanoprobe and a capture nanoprobe directed to a nucleic acid target in the presence and the absence of the target under conditions suitable for the target to hybridize with the capture nanoprobe, wherein the reporter nanoprobe comprises: at least one plasmonic nanoparticle; and an oligonucleotide reporter probe attached at one end to the nanoparticle, the reporter probe having an optical label;wherein the capture nanoprobe comprises: at least one plasmonic nanoparticle; and a capture oligonucleotide attached at one end to the nanoparticle, wherein the capture oligonucleotide is complementary to both the reporter probe and the nucleic acid target, and wherein the capture oligonucleotide hybridizes to the reporter probe in the absence of the nucleic acid target such that plasmonic coupling electromagnetic enhancement occurs between neighboring reporter and capture nanoparticles, irradiating the sample with electromagnetic radiation from an excitation source; and detecting the electromagnetic radiation originated by the label, wherein a level of electromagnetic radiation originated by the label in the presence of the target is changed upon hybridization of the capture oliognucleotide to the target.

The optical label can include a Raman dye, 3,3'-Diethylthiadicarbocyanine iodide (DTDC), 3,3'-diethylthiatricarbocyanine iodide (DTTC), 1,1',3,3,3',3'-Hexamethylindotricarbocyanine iodide (HITC), CY3 dye, CY3.5 dye, CY5.5 dye, CY7 dye, CY7.5 dye, a positively-charged hydrophobic near infrared (NIR) dye, IR-780, IR-792, IR-797, IR-813, methylene blue hydrate (MB), 4-mercaptobenzoic acid (4-MBA), 5,5'-dithiobis-2-nitrobenzoic acid (DTNB), 4-aminothiophenol (4ATP), fluorescein, fluorescein isothiocyanate (FITC), thionine dyes, rhodamine-based dye, crystal violet, a fluorescence label, or absorbance label.

In the method for detecting nucleic acid targets, detecting the electromagnetic radiation originated by the label can be by one or more of surface enhanced Raman scattering (SERS) detection, surface-enhanced resonance Raman scattering (SERRS), fluorescence detection and absorbance detection.

The nucleic acid target can be a biomarker for a disease or disorder. The disease or disorder can include one or more of cancer, breast cancer, traumatic brain injury, infectious disease, Alzheimer's disease, diabetes, and cardiovascular disease.

The nucleic acid target can include a DNA, an RNA, a microRNA, a mRNA, or a single polynucleotide polymorphism (SNP).

The plasmonic nanoparticle of the nanoprobes can include silver nanoparticles, gold nanoparticles, silver nanostars, gold nanostars, dielectric nanoparticle cores covered with metal nanoshells, or multi-nanoparticle structures. The plasmonic nanoparticle of the nanoprobes can be embedded within a protective coating. The protective coating can includes NIPAM. The plasmonic nanoparticle of the nanoprobes can be embedded within a hollow shell. The shell can include one or more of silica, polymer, and liposome.

In the method for detecting nucleic acid targets, the incubating can include at least a second pair of nanoprobes directed to a second nucleic acid target and the second reporter probe can include a second attached label. The detecting can be performed using multiplexing such that the first and the at least second targets can be detected simultaneously.

In the method for detecting nucleic acid targets, the reporter nanoprobe and the capture nanoprobes can each be further directed to at least a second, third and fourth nucleic acid target. The reporter nanoprobe can further include a second, third and fourth oligonucleotide reporter probe, and each of the second, third and fourth reporter probes can include a second, third and fourth attached label, respectively. The capture probe can include a second, third and fourth capture oligonucleotide complementary to both the second, third and fourth reporter probes, respectively, and the second, third and fourth nucleic acid targets, respectively. The detecting can be performed using multiplexing such that all of the four targets can be detected simultaneously.

In one embodiment, a method is provided for treating undesirable cells comprising: contacting an undesirable cell with a reporter nanoprobe and a capture nanoprobe, wherein the reporter nanoprobe comprises: at least one plasmonic nanoparticle; and an oligonucleotide reporter probe attached at one end to the nanoparticle, the reporter probe having an optical label;wherein the capture nanoprobe comprises: at least one plasmonic nanoparticle; and a capture oligonucleotide attached at one end to the nanoparticle, wherein the capture oligonucleotide is complementary to both the reporter probe and the nucleic acid target, and wherein the capture oligonucleotide hybridizes to the reporter probe in the absence of the nucleic acid target such that plasmonic coupling electromagnetic enhancement occurs between neighboring reporter and capture nanoparticles; and irradiating the sample with electromagnetic radiation from an excitation source, wherein the optical label is capable of absorbing electromagnetic radiation from one or both of electromagnetic radiation originated as a result of excitation of the nanoparticle and directly from the excitation radiation, and wherein the undesirable cells are damaged by one or both of thermal energy direct from the radiation and thermal energy emitted as a result of excitation of the nanoparticle.

In the method for treating undesirable cells, the optical label can include a Raman dye, 3,3'-Diethylthiadicarbocyanine iodide (DTDC), 3,3'-diethylthiatricarbocyanine iodide (DTTC), 1,1',3,3,3',3'-Hexamethylindotricarbocyanine iodide (HITC), CY3 dye, CY3.5 dye, CY5.5 dye, CY7 dye, CY7.5 dye, a positively-charged hydrophobic near infrared (NIR) dye, IR-780, IR-792, IR-797, IR-813, methylene blue hydrate (MB), 4-mercaptobenzoic acid (4-MBA), 5,5'-dithiobis-2-nitrobenzoic acid (DTNB), 4-aminothiophenol (4ATP), fluorescein, fluorescein isothiocyanate (FITC), thionine dyes, rhodamine-based dye, crystal violet, a fluorescence label, or absorbance label. The method can further include detecting the electromagnetic radiation originated by the optical label by one or more of surface enhanced Raman scattering (SERS) detection, surface-enhanced resonance Raman scattering (SERRS), fluorescence detection, and absorbance detection.

In the method for treating undesirable cells, the detecting of the electromagnetic radiation originated by the optical label can locate the targeted undesirable cells such that the irradiating can be better localized to the undesirable cells.

In the method for treating undesirable cells, the nanoparticle can include a protective layer surrounding the nanoparticle having within the layer one or more of a photosensitizer, a photoactivator, and a chemotherapy drug such that the photosensitizer, the photoactivator, and the chemotherapy drug is released or activated via one or more of passive diffusion release, photochemically triggered release, thermal triggered release, pH triggered release, photochemical activation, and thermal activation. The protective layer can include NIPAM.

In the method for treating undesirable cells, the undesireable cells can include cancer cells.

In one embodiment, a method is provided for detecting nucleic acid targets with a color change, comprising: incubating a reporter nanoprobe and a capture nanoprobe directed to a nucleic acid target in the presence and the absence of the target under conditions suitable for the target to hybridize with the capture nanoprobe, wherein the reporter nanoprobe comprises: at least one plasmonic nanoparticle; and an oligonucleotide reporter probe attached at one end to the nanoparticle; wherein the capture nanoprobe comprises: at least one plasmonic nanoparticle; and a capture oligonucleotide attached at one end to the nanoparticle, wherein the capture oligonucleotide is complementary to both the reporter probe and the nucleic acid target, and wherein the capture oligonucleotide hybridizes to the reporter probe in the absence of the nucleic acid target such that plasmonic coupling electromagnetic enhancement occurs between neighboring reporter and capture nanoparticles; and detecting a color change in the presence of the target due to separation of the reporter and capture nanoparticles upon binding of the target to the capture oligonucleotide. The color change can be a visible color change.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Preparation of Silver (Gold) Nanoparticles

Silver (or gold) colloids were prepared according to the standard Lee-Meisel method: 200 mL of $10^{-3}$ M $AgNO_3$ aqueous solution was boiled under vigorous stirring, then 5 mL of 35-mM sodium citrate solution were added and the resulting mixture was kept boiling for 1 h. This procedure was reported to yield ~$10^{11}$ particles/mL of homogenously sized colloidal particles with a diameter of ~35-50 nm and an absorption maximum at 390 nm. The colloidal solutions were stored at 4° C. and protected from room light. Further dilutions of the colloidal solutions were carried out using distilled water.

Example 2

Fabrication/preparation of Metal Nanocaps

The approach used involved the use of nanospheres spin-coated on a solid support in order to produce and control the desired roughness. The nanostructured support was subsequently covered with a layer of silver that provides the conduction electrons required for the surface plasmon mechanisms. Among the techniques based on solid substrates, the methods using simple nanomaterials, such as Teflon or latex nanospheres, appear to be the simplest to prepare. Teflon and latex nanospheres are commercially available in a wide variety of sizes. The shapes of these materials are very regular and their size can be selected for optimal enhancement. These materials consist of isolated dielectric nanospheres (30-nm diameter) coated with silver producing systems of half-nano shells, referred to as nanocaps. The nanoparticles can be sonicated to release them from the underlying substrate. The effect of the sphere size and metal layer thickness upon the SERS effect can be easily investigated. By rotating the platform supporting the nanospheres, one can extend the solver coverage and produce the "crescent structures" shown in FIG. 10. The silver coated nanospheres were found to be among the most plasmonics-active investigated. Gold can also be used instead of silver to coat over a nanoparticles materials.

Example 3

Fabrication of Gold Nanoshells

Gold nanoshells were prepared using the method described by Hirsch et al. [Hirsch L R, Stafford R J, Bankson J A, Sershen S R, Price R E, Hazle J D, Halas N J, West J L (2003) Nanoshell-mediated near infrared thermal therapy of tumors under MR Guidance. Proc Natl Acad Sci 100: 13549-13554]. A mechanism was used involving nucleation and then successive growth of gold nanoparticles around a silica dielectric core. Gold nanoparticles, the seed, prepared as described above using the Frens method, were used to grow the gold shell. Silica nanoparticles (100 nm) used for the core of the nanoshells were monodispersed in solution of 1% APTES in EtOH. The gold "seed" colloid synthesized using the Frens method were grown onto the surface of silica nanoparticles via molecular linkage of amine groups. The "seed" covers the aminated silica nanoparticle surface, first as a discontinuous gold metal layer gradually growing forming a continuous gold shell. Gold nanoparticles used as the "seed" were characterized using optical transmission spectroscopy (UV-Vis Spectrophotometer, Beckman Coulter, Fullerton, Calif.) and atomic force microscopy (Atomic Force Microscope, Veeco Instruments, Woodbury, N.Y.) while gold nanoshells were characterized using optical transmission spectroscopy and scanning electron microscopy (Scanning Electron Microscope, Hitachi S-4700, Hitachi High Technologies America, Inc. Pleasanton, N.Y.).

Example 4

Plasmonic Coupling Interference (PCI) Nanoprobes for Nucleic Acid Detection Using Surface-enhanced Raman Scattering (SERS).

A label-free approach is described using plasmonic coupling interference (PCI) nanoprobes for nucleic acid detection using surface-enhanced Raman scattering (SERS). To induce a strong plasmonic coupling effect, a nano-network of silver nanoparticles having the Raman label located between adjacent nanoparticles is assembled by Raman-labeled DNA-locked nucleic acid (LNA) duplexes. The PCI method then utilizes specific nucleic acid sequences of interest as competitor elements of the Raman-labeled DNA strands to interfere the formation of nano-networks in a competitive binding process. As a result, the plasmonic coupling effect induced through the formation of the nano-networks is significantly diminished, resulting in a reduced SERS signal. The utility of the PCI technique is demonstrated for biomedical applications by detecting single-nucleotide polymorphism (SNP) and microRNA sequences involved in breast cancers. The results of this study demonstrate the utility of the nanoprobes as nucleic acid diagnostic tools for biomedical diagnostics and biosensing applications using SERS detection.

The development of practical and sensitive techniques for screening nucleic acid biomarkers related to medical diseases and cancers is critical for early diagnosis, prevention and effective interventions. Recent advances in molecular profiling technology have made significant progress in the discovery of various biomarkers. It has been implicated that biomarkers such as single-nucleotide polymorphisms (SNPs) and microRNAs (miRNAs) could serve as important predictors of cancer risk and progression. SNPs are the most common genetic variations which could contribute to disease risk by creating genetic instability. MicroRNAs, a class of small noncoding endogenous RNA molecules, are emerging as promising biomarkers for cancer diagnostics and classification. Fast and precise measurement of SNPs and miRNAs will help identify molecular signatures critical for the evaluation of cancer risk and early detection.

It has been observed that metal nanoparticles usually aggregate in a high ionic strength salt solution. However, this aggregation process is generally uncontrollable, thus seriously affecting the reproducibility of SERS measurements. To practically control the separation distance between particles, DNA oligonucleotides have been utilized as spacers and linkers to assemble nanoparticles into a network of NPs in a controllable manner. Moreover, DNA sequences of interest have been designed as the interparticle linkers to induce the plasmonic coupling effect leading to an increased SERS signal of the Raman reporters absorbed on the Au nanoparticle surface.

In this experiment, a new approach is described referred to as plasmonic coupling interference (PCI) for DNA/RNA detection using SERS. The PCI method described herein below combines the plasmonic coupling phenomenon with the nucleic acid hybridization process, leading to the development of a label-free (i.e., the targets do not need to be labeled) detection approach for DNA/RNA target. The PCI method utilizes specific DNA sequences of interest to induce interference in the plasmonic coupling effect. As a result, the reduction in SERS intensity of Raman-labeled DNA probes can be used as a parameter for a new biosensing modality.

The nanoprobes and PCI method using functionalized silver NPs is illustrated in FIG. 1. In this approach, nanoparticles were coupled using the shortest separation distance in order to induce a strongest plasmonic coupling and a maximum SERS enhancement of a Raman label located between two adjacent silver nanoparticles. Previous studies have shown that nanoparticles can be coupled using DNA oligonucleotides with over 8 bases. However, due to the thermal instability of short DNA-DNA duplexes, it is difficult to use DNA oligonucleotides shorter than 8 bases for assembling nanoparticles into a nano-network. To overcome this problem, short locked nucleic acids (LNAs) with 7 bases were ultilized in order to couple nanoparticles in a separation distance between 2 to 3 nm. It has been previously reported that LNAs can offer a high salt and thermal stability for coupling nanoparticles. Nonetheless, longer LNA or DNA oligonucleotides were also tested in this study, e.g. 17-base probes for SNP detection, and 22-base probes for miRNA detection.

Silver NPs were first functionalized with 0.5-μm thiolated LNAs with the sequence of 5'-dithiol-GGGCGGG-3' (referred to herein as capture-NPs) and with the complementary dye-labeled probes with the sequence of 3'-CCCG(Cy3)CCC-dithiol-5' (referred to herein as reporter-NPs). A Raman dye, Cy3, was used as the signal reporter, which was internally attached to the guanine (G-base) in the middle of the reporter oligonucleotide. However, the labeling site is not restricted to the middle of the oligonucleotides. The Raman dye can also be labeled at the 3'-end. These functionalized NPs (both capture-NPs and reporter-NPs) were then further conjugated with low molecular weight thiolated poly(ethylene glycol)s (HS-PEGs). It has been indicated that short PEGs can provide the silver NPs stability in sodium phosphate buffer solution containing 100 mM NaCl. The number of labeled-oligonucleotides immobilized on a silver NP was estimated to be ~220 oligonucleotides per particle for the 7-base dithiol probes, ~130 oligonucleotides per particle for the 17-base dithiol probes, and ~300 oligonucleotides per particle for the 13-base alkanethiol probes.

To induce plasmonic coupling effect, capture-NPs and reporter-NPs were mixed in a volume ratio of 1:1 in order to form LNA-DNA duplexes. The mixture was allowed to react at room temperature for 20 min in a 10-mM Tris-HCl buffer solution (pH 8.0) containing 50 mM NaCl and 2.5 mM $MgCl_2$. The duplex formation assembled nanoparticles into a three-dimensional nano-network of NPs having the Cy3 label located between adjacent NPs. In this situation the Cy3 label molecules experience a strong plasmonic coupling effect, leading to an increased SERS signal of the Raman labels upon laser excitation. In this approach, the sequences of DNA probes (reporter-NPs) are designed to have the same sequence as the DNA targets. Therefore, the target DNA strands are then used as competitors of the reporter-NPs in a competitive binding process. As a result, the SERS signal is not enhanced since the plasmonic coupling is interfered with by the target strands.

FIGS. 7A-7B show the increased SERS intensity of the Cy3 Raman peaks in the presence of both capture-NPs and reporter-NPs (FIG. 7A) as compared to the SERS intensity in the presence of target DNA strands (FIGS. 7B). The enhanced SERS signal indicates that the plasmonic coupling was induced by the hybridization reaction between the LNA and the labeled-DNA strands. To demonstrate the detection of DNA by using the nanoprobes and method of plasmonic coupling interference, capture-NPs and target DNA strands (1 μM) were mixed 1 hour prior to addition of a solution of reporter-NPs in order to ensure that the target DNA can effectively react with LNA strands. After adding reporter-NPs, the mixture was allowed to react for 20 min at room temperature and immediately followed by SERS measurements without washing steps. The spectrum in FIG. 7B shows the quenched SERS signal in the presence of target DNA strands in the mixture of capture-NPs and reporter-NPs, thus indicating that the plasmonic coupling effect was interfered with in the presence of target DNA strands.

Time-dependent monitoring of the nucleic acid-cross-linked silver-NP aggregates was performed using the absorption spectroscopy by mixing capture-NPs and reporter-NPs (data not shown). After a 10 min reaction time, it was found that the surface plasmon band was red-shifted from ~400 to ~700 nm, indicating that silver NPs were aggregated via nucleic acid hybridization. This result indicates the utility of this approach as a simple and rapid screening tool based on simple visual examination of color changes of the sample.

Quantitative Analysis. The capability for quantitative analysis is an important feature of any bioanalytical technique. In this experiment the quantitative aspects of nanoprobe detection was investigated. In a series of measurements, the concentration of the capture-NPs and reporter-NPs was held constant and the concentration of target DNA wa varied from 0 to 1 μm. FIG. 8 shows that the SERS intensity of reporter-NPs at 1195 $cm^{-1}$ decreased with increasing target DNA concentrations indicating that plasmonic coupling effect between capture-NPs and reporter-NPs was interfered with to different degrees by changes in the concentration of target DNA competitors. The minimum target DNA concentration that can cause detectable interference in the current unoptimized system is about 200 pM with the dynamic range from 200 pM to 100 nM. The results of this study demonstrate the utility of nanoprobes and methods for quantitative nucleic acid diagnostics.

Single-Nucleotide Polymorphism (SNP) Detection. To demonstrate the biomedical application of the nanoprobes and detection methods for SNP detection, a pair of capture-NPs and reporter-NPs with the sequence of 5'-dithiol-$A_{10}$-GACGGAC-3' (Val654-capture with LNA bases underlined) and 3'-Cy3-CTGCCTG-$A_{10}$-dithiol -5' (Val654-reporter with Cy3 labeling at 3'-end), respectively, were designed to detect a rare single-nucleotide polymorphism (SNP) (Ile654Val) of the ERBB2 gene. The ERBB2 gene (also known as HER2/neu) belonging to the epidermal growth factor receptor (EGFR) family is well known as a critical biomarker for breast cancer. The Ile654Val SNP linked to another more frequent Ile655Val SNP resides within the transmembrane domain. It has been suggested that the rare ERBB2 variant Ile654Val is associated with an increased familial breast cancer risk. However, due to the close vicinity of the Ile654Val and Ile655Val SNPs, it is difficult to detect the Ile654Val SNP by using DNA probes such as TaqMan probes.

Figure 13A:
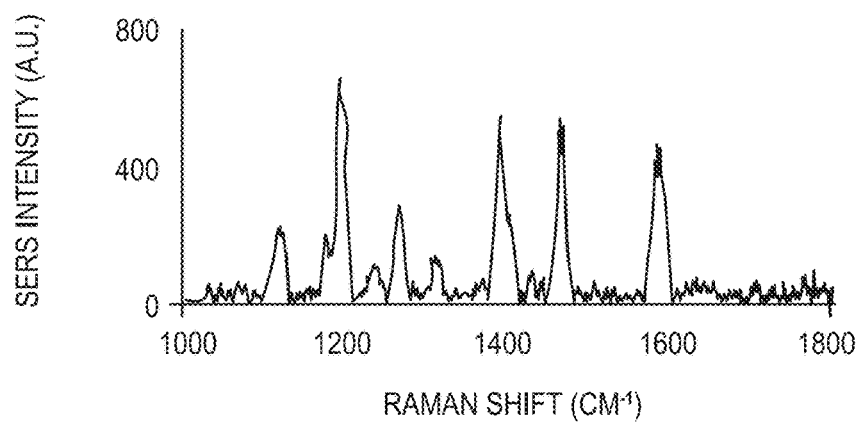
FIGS. 13A-13C are SERS spectra of nanoprobes with a Raman dye label in the presence and absence of a single nucleotide polymorphism (SNP) ERBB2 Ile654Val target DNA according to embodiments of the present disclosure. A) SERS spectra for a mixture of Val654-reporter-NPs and Val654-capture-NPs in the absence of SNP target DNA. B) SERS spectra for a mixture of Val654-reporter-NPs and Val654-capture-NPs in the presence of 10 nM wild-type sequences. C) SERS spectra for a mixture of Val654-reporter-NPs and Val654-capture-NPs in the presence of 10 nM SNP target sequences showing the absence of Raman peaks.
Figure 13B:
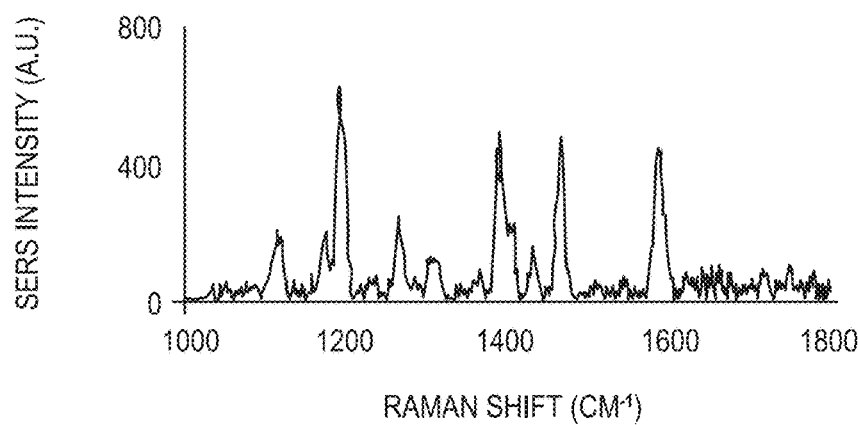
Figure 13C:
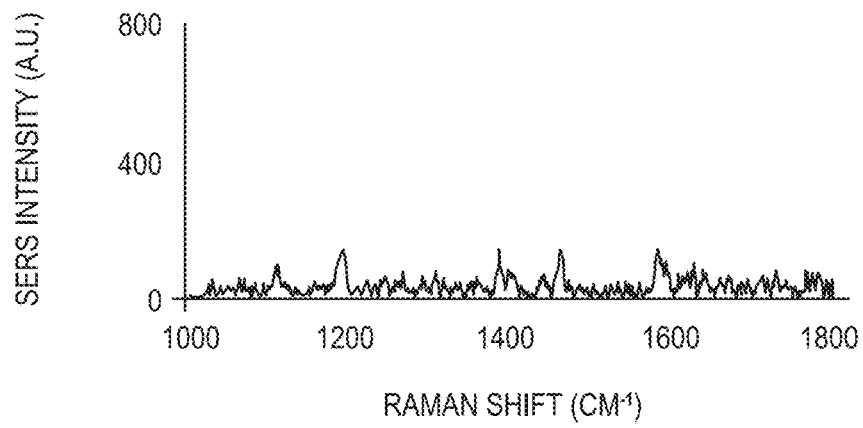

To overcome this difficulty, the 7-base LNA (Val654-capture) complementary to the Ile654Val SNP sequence was used to increase single nucleotide discrimination. As shown in FIG. 13C, the reduction in SERS intensity indicates that the plasmonic coupling effect was significantly interfered with in the presence of 10 nM SNP sequences (5'-GTC-CGTC-3'). However, in the blank sample (FIG. 13A) or in the presence of 10 nM wild-type sequences (FIG. 13B; 5'-GTCCATC-3'), the SERS signals were enhanced in both cases indicating that the plasmonic coupling effect was induced through the formation of nano-networks composed of the Val654-capture-NPs and Val654-reporter-NPs. The result of this study demonstrates that the nanoprobes and methods of the present disclosure can be used as tools to identify SNPs for medical diagnostics of significance.

MicroRNA Detection. To illustrate the use of the nanoprobes and methods of the present disclosure for biomedical diagnostics, the methods were applied to the detection of miRNA samples. The miRNA is a class of 18-24 nucleotide non-coding RNA molecules found in almost all organisms, including humans, plants, virus and animals. Recent studies revealed that miRNAs exert their gene regulatory function either directly through cleavage of messenger RNA (mRNA) or indirectly through translational repression by binding to their target mRNA strands. It has been shown that miRNAs are involved in many critical biological processes such as development, differentiation, metabolism and tumorigenesis. Moreover, alterations in the expression levels of a single or multiple miRNAs have been shown to be linked with cancer types, disease stages and response to treatment. The miRNA expression profiles may serve as useful tests for cancer and disease diagnostics. In the past years, many miRNA detection methods have been reported. However, the small size of miRNA molecules makes the detection more difficult than working with genomic DNA and mRNA. So far, the most standardized and widely used method to detect miRNA is northern blotting, which is laborious and time-consuming. Thus, there is a strong need to develop a rapid, selective and sensitive method to detect miRNA molecules.

Figure 14A:
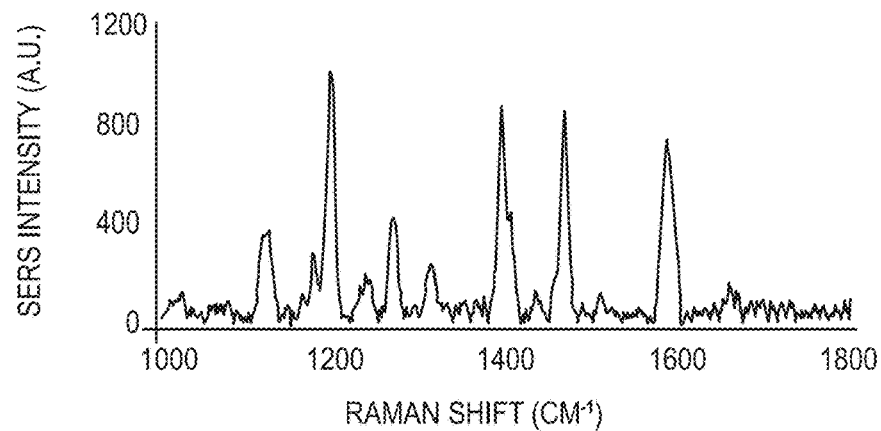
FIGS. 14A-14C are SERS spectra of nanoprobes with a Raman dye label in the presence and absence of a MicroRNA miR21 target according to embodiments of the present disclosure. A) SERS spectra for a mixture of miR21-reporter-NPs and miR21-capture-NPs. B) SERS spectra for a mixture of miR21-reporter-NPs and miR21-capture-NPs in the presence of 100 nM non-complementary DNA. C) SERS spectra for a mixture of miR21-reporter-NPs and miR21- capture-NPs in the presence of 100 nM complementary miRNA target showing the absence of Raman peaks.
Figure 14B:
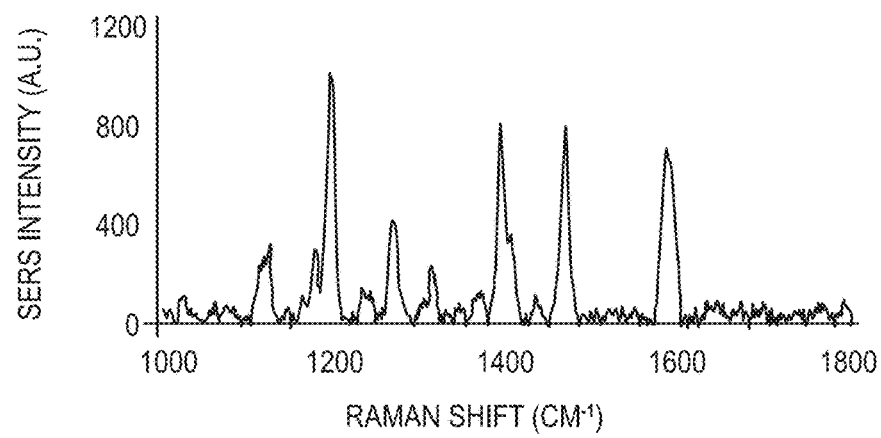
Figure 14C:
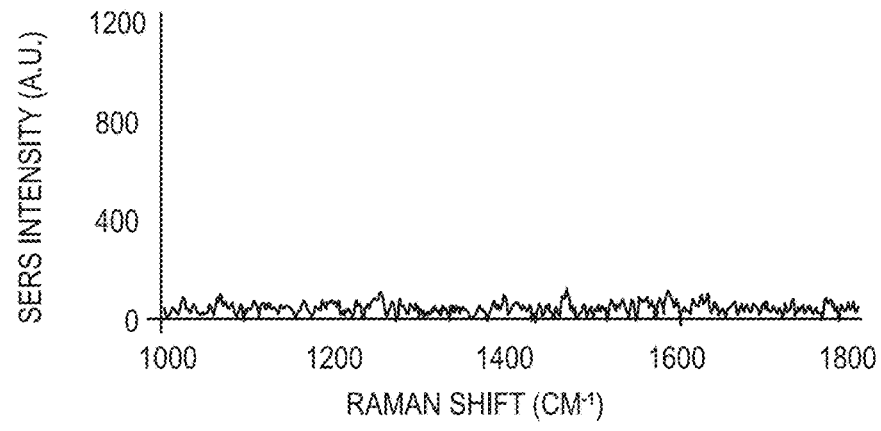

To demonstrate the detection of miRNAs using the nanoprobes and methods of the present disclosure, a pair of unlabeled complementary probes (capture-(miR21)-NPs) and Cy3-labeled probes (reporter-(miR21)-NPs) with the sequences of 5'-SH-TCAACATCAGTCTGATAAGCTA-3' (SEQ ID NO: 1) and 5'-SH-TAGCTTATCAGAC-Cy3-3' (SEQ ID NO: 2), respectively, were designed to detect the mature human miRNA-21 (miR-21) molecules with sequences of 5'-UAGCUUAUCAGACUGAUGUUGA-3' (SEQ ID NO: 3). It has been shown that miR-21 functions as an oncogene and is overexpressed in a variety of different tumors including breast cancers. The unlabeled capture-(miR21)-probes are fully complementary to the mature miR-21 sequences, and the Cy3-labeled reporter-(miR21)-probes are complementary to a partial sequence of the unlabeled capture-(miR21)-probes. The melting temperature for the duplex of the capture-(miR21)-probes and Cy3-labeled reporter-(miR21)-probes is estimated at 33.4° C. in a 50-mM NaCl solution. Thus, the hybridization-mediated nanoparticle aggregation could be expected to take place at room temperature. The nanoprobes and methods of the present disclosure were designed for detection of miR-21 using synthesized miRNA with sequence of 5'-UAGC-UUAUCAGACUGAUGUUGA-3' (SEQ ID NO: 3) as the target molecules. As shown in the spectrum of FIG. 14C, the reduction in SERS intensity indicates that the plasmonic coupling effect was significantly interfered with in the presence of 100 nM complementary miR-21 targets. However, in the absence of target miRNA sample (FIG. 14A) or in the presence of 100 nM non-complementary DNA samples with sequence of 5'-TCATCCATGACAACTTTG-GTATCGTGGAAGGACTCATGAC-3' (SEQ ID NO: 4) (FIG. 14B; negative control), the SERS signals were enhanced in both cases indicating that the plasmonic coupling effect was induced through the aggregated nanoparticles. The result of this study demonstrates that the nanoprobes and methods of the present disclosure can be used as a tool to detect miRNA molecules for medical applications.

A label-free approach for SERS-based nucleic acid detection has been demonstrated with the nanoprobes and methods of the present disclosure utilizing target oligonucleotides as competitive binding products to interfere with plasmonic coupling effect in nano-networks. In the studies described above, 7-base LNAs were developed and used to demonstrate the capability for coupling nanoparticles in a very short separation distance with high thermal stability. It was demonstrated that the methods can be used to identify and discriminate DNA sequences with SNPs. Moreover, it was demonstrated that the methods can be used to detect specific miRNA sequences as a simple and rapid screening tool for cancer diagnosis. Furthermore, the highly specific and narrow SERS spectral peaks allow for multiple assays to be performed simultaneously in a single sample solution when using multiple Raman labels. There is a strong need for nucleic acid bioassays that are label-free and can be used in a variety of applications ranging from biomedical diagnostics, food safety, environmental monitoring and homeland defense. The results of demononstrate the utility of the nanoprobes and methods of the present disclosure for such nucleic acid diagnostic tools for a wide variety of applications based on nucleic acid detection to address the above sensing needs.

Materials: Silver nitrate (99.995%) was purchased from Alfa Aesar (Ward Hill, Mass.). Hydroxylamine hydrochloride and sodium hydroxide, pellet were purchased from Mallinckrodt Baker, Inc (Phillipsburg, N.J.), mPEG-SH (O-(2-Mercaptoethyl)-O'-methyl-hexa(ethylene glycol)), and Tris-HCl buffer (1M, pH 8.0) were purchased from Sigma-Aldrich. All solution was prepared with deionized water (18 MΩ-cm). All DNA and LNA oligonucleotides were synthesized and purchased from Integrated DNA Technologies, Inc (Coralville, Iowa).

Preparation of silver nanoparticles: The silver nanoparticles were prepared by using hydroxylamine hydrochloride as the reduction agent described previously. Briefly, a silver nitrate solution (10 mL of a $10^{-2}$ M solution) was rapidly added to a hydroxylamine hydrochloride solution (90 mL of a $1.67 \times 10^{-3}$ M solution) containing NaOH ($3.3 \times 10^{-3}$ M) under vigorous stirring for one hour. The colloidal solutions were then stored at 4° C. and used within a few days. The size of Ag NPs was determined to have an average diameter of 35±6.3 nm using transmission emission microscopy (TEM) (data not shown). The quantity of the nanoparticles was estimated to be ~$4.8 \times 10^{11}$ particles/mL measured by using NanoSight NS500 (NanoSight Ldt. Amesbury, UK), and ~18.5 $cm^2$/mL surface area available for oligonucleotides to bind to nanoparticles.

Synthesis of oligonucleotide-conjugated silver nanoparticles: Silver nanoparticles (1 mL) were first incubated with thiolated DNA or LNA oligonucleotides (0.5 µM) in 0.25 mM $MgCl_2$ for overnight at room temperature. To stabilize the nanoparticles, mPEG-SH (20 µM) was then added to the solution for 10 min. The functionalized nanoparticles were washed with Tris-HCl buffer (10 mM, pH 8.0) containing Tween 20 (0.01%) using repeated centrifugation at 12,000 rpm for 10 min. The purified nanoparticles were finally resuspended in Tris-HCl buffer (1 mL of a 10 mM buffer solution, pH 8.0) containing Tween 20 (0.01%).

Quantification of oligonucleotides immobilized on silver nanoparticles: The number of oligonucleotides bound to a silver nanoparticle was then determined by a ligand exchange process described previously. Briefly, the dye-labeled reporter-NPs were incubated with Mercaptoethanol (0.5 M) for 16 hours at room temperature to release dye-labeled oligonucleotides from the nanoparticle surface. The solutions were centrifuged at 12,000 rpm for 10 min to isolate the Ag NPs. The fluorescence emission of the collected supernatants was then measured using the FLUOstar Omega microplate reader (BMG Labtech, Inc.). The supernatants were excited at 550 nm and the emission was collected at 590 nm. The concentrations of the released reporter oligonucleotides were determined according to a standard curve. The number of oligonucleotides per particle was then determined by dividing the total number of bound oligonucleotides by the number of nanoparticles. The experiment was repeated three times using fresh samples.

SERS measurements: SERS measurements were performed using a Renishaw InVia confocal Raman microscope equipped with a 50 mW HeNe laser emitting a 632.8 nm laser line for excitation, a holographic notch filter used to block light due to Rayleigh scatter, and an 1800 groove/mm grating used to provide a spectral resolution of 1 $cm^{-1}$. By using a 10× microscope objective, the laser was focused into a 100 µL sample solution in a glass vial. The Raman scattered light was collected by the same objective, and detected by a 1024×256 pixel RenCam CCD detector.

Any patents or publications mentioned in this specification are indicative of the levels of those skilled in the art to which the present disclosure pertains. These patents and publications are herein incorporated by reference in their entirely to the same extent as if each individual publication was specifically and individually indicated to be incorporated by reference.

One skilled in the art will readily appreciate that the present present disclosure is well adapted to carry out the objects and obtain the ends and advantages mentioned, as well as those inherent therein. The present examples along with the methods described herein are presently representative of preferred embodiments, are exemplary, and are not intended as limitations on the scope of the invention. Changes therein and other uses will occur to those skilled in the art which are encompassed within the spirit of the present disclosure as defined by the scope of the claims.

We claim:

1. A plurality of a pair of nanoprobes for detecting a nucleic acid target, wherein the nucleic acid target is a DNA, RNA, microRNA, mRNA, or single polynucleotide polymorphism (SNP) biomarker that has been correlated to one or more human diseases or disorders selected from cancer, breast cancer, traumatic brain injury, infectious disease, Alzheimer's disease, diabetes, or cardiovascular disease, the pair of nanoprobes comprising a reporter nanoprobe and a capture nanoprobe, wherein the reporter nanoprobe comprises:
   i. at least one reporter plasmonic silver nanoparticle, wherein a distance between two diametrically opposed points on an outer edge of the plasmonic silver nanoparticle is 30-50 nm; and
   ii. a plurality of a reporter oligonucleotide attached to the reporter nanoparticle and having an attached Raman dye label, wherein the reporter oligonucleotide ranges in length from 7 to 22 nucleotides, and wherein the capture nanoprobe comprises:
   i. at least one capture plasmonic silver nanoparticle, wherein a distance between two diametrically opposed points on an outer edge of the plasmonic silver nanoparticle 30-50 nm; and
   ii. a plurality of a capture locked nucleic acid (LNA) or a capture oligonucleotide attached at one end to the capture nanoparticle, wherein the capture LNA or capture oligonucleotide is complementary to both the reporter oligonucleotide and the nucleic acid target and ranges in length from 7 to 22 nucleotides, and wherein the capture LNA or capture oligonucleotide hybridizes to the reporter oligonucleotide in the absence of the nucleic acid target such that plasmonic coupling electromagnetic enhancement occurs between neighboring reporter and capture nanoparticles.

2. The nanoprobes of claim 1, wherein the plasmonic silver nanoparticle comprises silver nanostars.

3. The nanoprobes of claim 2, wherein one or both of the plasmonic silver nanoparticles is embedded within a coating comprising N-isopropylacrylamide (NIPAM).

4. The nanoprobes of claim 1, wherein the one or both of the plasmonic silver nanoparticles is embedded within a hollow shell comprising silica.

5. The nanoprobes of claim 1, wherein a primer pair has a sequence selected from SEQ ID NO: 1 and SEQ ID NO: 2.

6. The nanoprobes of claim 5, wherein the target is mature human miRNA-21.

7. The nanoprobes of claim 6, where the target has the sequence set forth in SEQ ID NO: 3.

8. The nanoprobes of claim 5, wherein the target is non-complementary DNA with the sequence set forth in SEQ ID NO: 4.

9. The nanoprobes of claim 1, wherein the nanoprobes are embedded into a N-isopropylacrylamide (NIPAM) hydrogel implant.

10. A plurality of a pair of nanoprobes for detecting a nucleic acid target, wherein the nucleic acid target is selected from:
   i. human radical S-adenosyl methionine domain containing 2 (RSAD2) gene that has been correlated to one or more of human cytomegalovirus, influenza virus, hepatitis C virus, dengue virus, alphaviruses, and retroviruses;
   ii. one or more *E. coli* serotype O157:H7 genes selected from rfbE, fliC, and mobA;
   iii. one or *Staphylococcus aureus* or *Staphylococcus epidermidis* genes selected from mecA and femA;
   iv. *Erwinia* herbicola 16S rRNA aroQ gene;
   v. one or more of *Bacillus anthracis* anthrax toxin activator (atxA) and protective antigen (PA) genes; or
   vi. combinations thereof;

wherein the pair of nanoprobes comprising a reporter nanoprobe and a capture nanoprobe;

wherein the reporter nanoprobe comprises:
   i. at least one reporter plasmonic silver nanoparticle, wherein a distance between two diametrically opposed points on an outer edge of the plasmonic silver nanoparticle is 30-50 nm; and
   ii. a plurality of a reporter oligonucleotide attached to the reporter nanoparticle and having an attached Raman dye label, wherein the reporter oligonucleotide ranges in length from 7 to 22 nucleotides, and wherein the capture nanoprobe comprises:
   i. at least one capture plasmonic silver nanoparticle, wherein a distance between two diametrically opposed points on an outer edge of the plasmonic silver nanoparticle is 30-50 nm; and
   ii. a plurality of a capture locked nucleic acid (LNA) or a capture oligonucleotide attached at one end to the capture nanoparticle, wherein the capture LNA or capture oligonucleotide is complementary to both the reporter oligonucleotide and the nucleic acid target and ranges in length from 7 to 22 nucleotides, and wherein the capture LNA or capture oligonucleotide hybridizes to the reporter oligonucleotide in the absence of the nucleic acid target such that plasmonic coupling electromagnetic enhancement occurs between neighboring reporter and capture nanoparticles.

11. The nanoprobes of claim 10, wherein the plasmonic silver nanoparticle comprises silver nanostars.

12. The nanoprobes of claim 11, wherein one or both of the plasmonic silver nanoparticles is embedded within a coating comprising N-isopropylacrylamide (NIPAM).

13. The nanoprobes of claim 10, wherein the nanoprobes are embedded into a N-isopropylacrylamide (NIPAM) hydrogel implant.

14. The nanoprobes of claim 10, wherein the one or both of the plasmonic silver nanoparticles is embedded within a hollow shell comprising silica.

* * * * *